(12) United States Patent
Noda et al.

(10) Patent No.: US 8,558,054 B2
(45) Date of Patent: Oct. 15, 2013

(54) ABSORBENT ARTICLE

(75) Inventors: Yuki Noda, Kagawa (JP); Kenichiro Kuroda, Kagawa (JP); Kumiko Nishikawa, Kagawa (JP)

(73) Assignee: Uni-Charm Corporation, Shikokuchuo-Shi, Ehime (JP)

( * ) Notice: Subject to any disclaimer, the term of this patent is extended or adjusted under 35 U.S.C. 154(b) by 638 days.

(21) Appl. No.: 12/527,534

(22) PCT Filed: Mar. 21, 2008

(86) PCT No.: PCT/JP2008/055299
§ 371 (c)(1),
(2), (4) Date: Dec. 9, 2009

(87) PCT Pub. No.: WO2008/117755
PCT Pub. Date: Oct. 2, 2008

(65) Prior Publication Data
US 2010/0121296 A1    May 13, 2010

(30) Foreign Application Priority Data
Mar. 26, 2007  (JP) .................. 2007-079929

(51) Int. Cl.
*A61F 13/15*  (2006.01)
*A61F 13/20*  (2006.01)

(52) U.S. Cl.
USPC .............. 604/380; 604/385.02; 604/385.201

(58) Field of Classification Search
USPC ................ 604/385.02, 385.201, 378–380
See application file for complete search history.

(56) References Cited

U.S. PATENT DOCUMENTS

| | | | |
|---|---|---|---|
| 4,333,463 A | | 6/1982 | Holtman |
| 4,592,751 A | * | 6/1986 | Gegelys ................ 604/368 |
| 4,676,784 A | | 6/1987 | Erdman et al. |
| 5,593,399 A | * | 1/1997 | Tanzer et al. ............ 604/368 |
| 2007/0078425 A1 | * | 4/2007 | Pateras et al. ........ 604/385.201 |

FOREIGN PATENT DOCUMENTS

| | | |
|---|---|---|
| EP | 1110528 | 6/2001 |
| EP | 1275362 | 1/2003 |
| JP | 9-504207 A | 4/1997 |

(Continued)

OTHER PUBLICATIONS

EP Search Report for EP 08722651 dated Mar. 23, 2010.

(Continued)

*Primary Examiner* — Elizabeth Houston
*Assistant Examiner* — Aundria Hairell
(74) *Attorney, Agent, or Firm* — Lowe Hauptman & Ham, LLP

(57) ABSTRACT

An absorbent body material article includes an absorbent article main unit, an absorbent body material included in the absorbent article main unit and including absorbent fibers and a super absorbent resin, and interspersed sections in the absorbent body material and having a longitudinal direction, a lateral direction, and a thickness direction. A densely gathered state of the absorbent fibers in each of the interspersed sections is less dense than a densely gathered state of the absorbent fibers around each of the interspersed sections. An occupied volume ratio of the super absorbent resin in the interspersed sections is greater than an occupied volume ratio of the super absorbent resin around the interspersed sections. At least one of the interspersed sections overlaps a fold line and the longitudinal direction of the at least one of the interspersed sections is aligned with the fold line.

10 Claims, 10 Drawing Sheets

(56) References Cited

FOREIGN PATENT DOCUMENTS

| | | |
|---|---|---|
| JP | 2001-252301 A | 9/2001 |
| JP | 2006-061396 A | 3/2006 |
| WO | 9522952 | 8/1995 |
| WO | 9606590 | 3/1996 |
| WO | 0021477 | 4/2000 |

OTHER PUBLICATIONS

PCT/JP2008/055299 International Search Report.

* cited by examiner

ABSORBENT ARTICLE

The present application is bvased on, International Application PCT/JP 2008/055299, filed Mar. 21, 2008 which claims priority from, Japan Application Number 2007-079929, filed Mar. 26, 2007, the disclosures of which are hereby incorporated by reference herein in their entirety.

TECHNICAL FIELD

The present invention relates to absorbent articles. In particular, the present invention relates to an absorbent article in which a fold line is formed when the absorbent article is folded for wrapping, the absorbent article including an absorbent body material in which areas where super absorbent resin is densely gathered are interspersed.

BACKGROUND ART

An absorbent article having an absorbent body material including a super absorbent resin for absorbing a predetermined fluid and the like is already known. Some such absorbent articles include an absorbent body material having interspersed sections that are interspersed, and in which the super absorbent resin is densely gathered. (see JP H9-504207A)

DISCLOSURE OF INVENTION

When the absorbent article is shipped, a folding process for wrapping is performed on the absorbent article. After fold lines are formed in predetermined positions in the absorbent article by this folding process, the absorbent article is wrapped. Naturally, it is desirable that the folding process can be easily performed, and also from the viewpoint of speeding up the wrapping process, it is necessary that the absorbent article can be easily folded at the positions where the fold lines are formed.

The present invention was made in view of these problems, and it is an advantage thereof to provide an absorbent article for which a folding process for wrapping can be performed more easily.

In order to solve the above-described problems, a principal aspect of the invention is an absorbent article that is used in a state in which the absorbent article contacts a body of a wearer on a skin face side, including: an absorbent article main unit; an absorbent body material that is included in the absorbent article main unit and that includes an absorbent fiber and a super absorbent resin; and interspersed sections that are included in the absorbent body material and that have a longitudinal direction, a lateral direction, and a thickness direction, wherein a densely gathered state of the absorbent fiber in each of the interspersed sections is less dense than a densely gathered state of the absorbent fiber around each of the interspersed sections, and an occupied volume ratio of the super absorbent resin in the interspersed sections is greater than an occupied volume ratio of the super absorbent resin around the interspersed sections, the absorbent article has a fold line for wrapping, and when the absorbent article is viewed from the skin face side, at least one of the interspersed sections overlaps the fold line in a state in which the longitudinal direction of the at least one of the interspersed sections is aligned with the fold line.

Other features of the invention will become clear by reading the description of the present specification with reference to the accompanying drawings.

Figure 1:
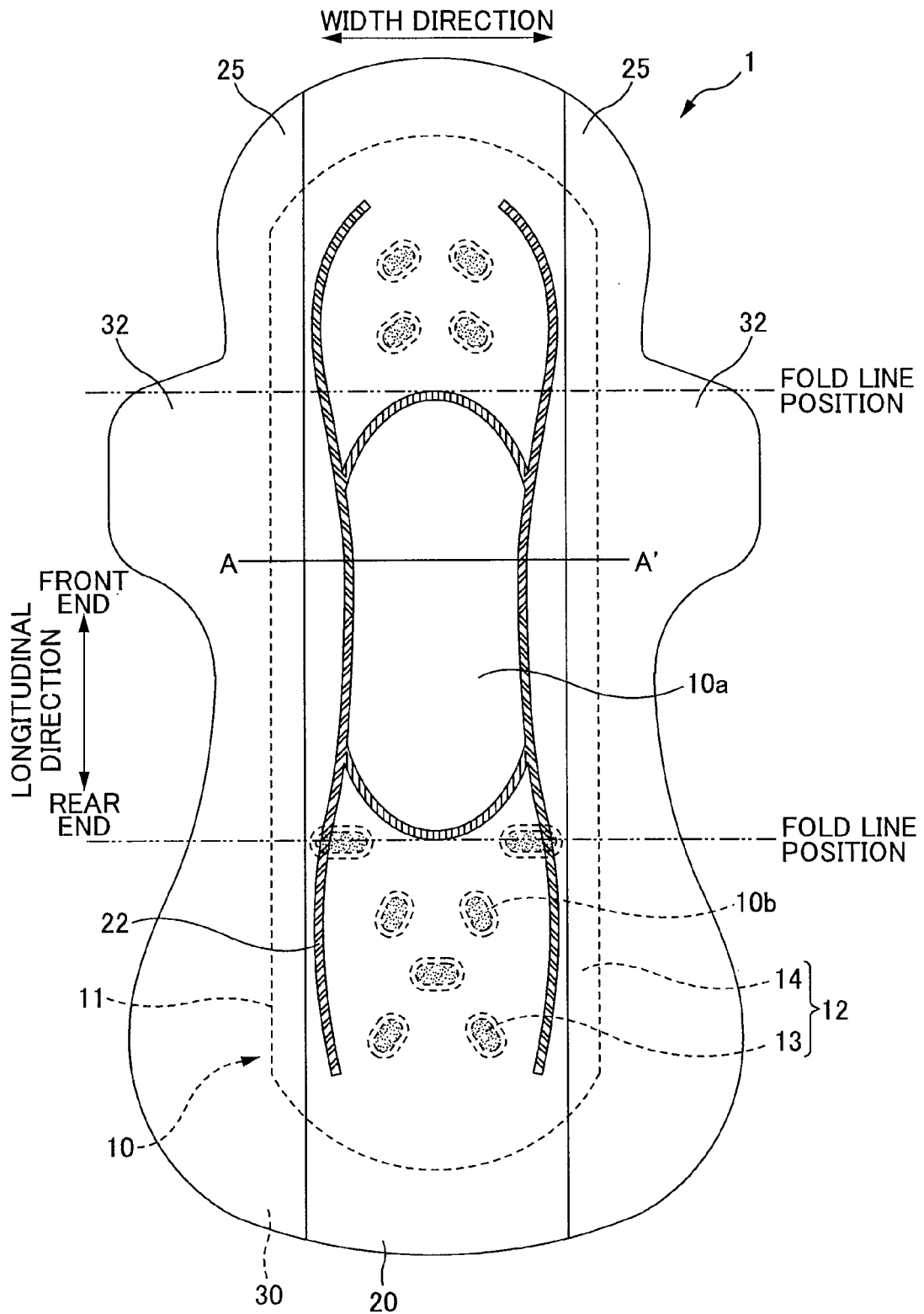
FIG. 1 is a schematic plan view that shows the configuration of an absorbent article 1.

LIST OF REFERENCE NUMERALS 1 absorbent article, 10 absorbent body, 10a swelling section,
10b surrounding section, 11 thin paper (covering member),
12 absorbent body material, 13 interspersed section,
13a densely gathered layer, 13b empty layer,
13c accumulated layer, 14 continuous section,
14a thick wall section, 14b channel section, 15 base material,
15a hole section, 20 surface sheet, 22 deep channel section,
25 side sheet, 30 back face sheet (absorbent article main unit),
31 joining section, 32 holding section, 34 releasing sheet,
35 adhesive, 36 wrapping sheet, 36a front end, 36b rear end,
38 lead tape, 80 absorbent body cutter, 82 product cutter

BEST MODE FOR CARRYING OUT THE INVENTION

At least the following matters will be made clear by reading the description of the present specification with reference to the accompanying drawings.

Firstly, an absorbent article that is used in a state in which the absorbent article contacts a body of a wearer on a skin face side, including: an absorbent article main unit; an absorbent body material that is included in the absorbent article main unit and that includes an absorbent fiber and a super absorbent resin; and interspersed sections that are included in the absorbent body material and that have a longitudinal direction, a lateral direction, and a thickness direction, wherein a densely gathered state of the absorbent fiber in each of the interspersed sections is less dense than a densely gathered state of the absorbent fiber around each of the interspersed sections, and an occupied volume ratio of the super absorbent resin in the interspersed sections is greater than an occupied volume ratio of the super absorbent resin around the interspersed sections, the absorbent article has a fold line for wrapping, and when the absorbent article is viewed from the skin face side, at least one of the interspersed sections overlaps the fold line in a state in which the longitudinal direction of the at least one of the interspersed sections is aligned with the fold line.

In such an absorbent article, the rigidity of each portion in the absorbent body material depends on the densely gathered state of the absorbent fiber accumulated in that portion. Therefore, the rigidity of the interspersed section, where the densely gathered state of the absorbent fiber is less dense, is less than an area around the interspersed section. When the absorbent article is viewed from a side in which the absorbent body material is provided, the interspersed section overlaps the fold line in a state in which the longitudinal direction of the interspersed section is aligned with the fold line. With such a configuration, compared with cases in which the lateral direction of the interspersed section is aligned with the fold line, or in which neither the longitudinal direction nor the lateral direction is aligned with the fold line, it is easier to fold the absorbent article so as to form the fold line. That is, an absorbent article is provided on which a folding process for wrapping can be performed more easily.

Alternatively, an absorbent article that is used in a state in which the absorbent article contacts a body of a wearer on a skin face side, including: an absorbent article main unit; an absorbent body material that is included in the absorbent article main unit and that includes an absorbent fiber and a super absorbent resin; and interspersed sections that are included in the absorbent body material and that have a longitudinal direction, a lateral direction, and a thickness direction, wherein the absorbent body material has a longitudinal direction, a lateral direction, and a thickness direction, the interspersed sections each includes a densely gathered layer in which super absorbent resin is densely gathered, and an empty layer that is adjacent to the densely gathered layer in the thickness direction of the absorbent body material, and when the absorbent article is viewed from the skin face side, at least one of the interspersed sections overlaps the fold line in a state in which the longitudinal direction of the at least one of the interspersed sections is aligned with the fold line.

In such an absorbent article as well, the rigidity of the interspersed section is less than the area around the interspersed section since the empty layer is included in the interspersed section. When the absorbent article is viewed from the skin face side, the interspersed section overlaps the fold line in a state in which the longitudinal direction of the interspersed section is aligned with the fold line. Therefore, for the reason stated above, it is easier to fold the absorbent article so as to form the fold line. As a result, an absorbent article is provided on which the folding process for wrapping can be performed more easily.

Also, in a configuration in which the densely gathered layer and the empty layer is provided in the interspersed section, the absorbent body material may include the absorbent fiber, and the absorbent fiber may be accumulated around the interspersed sections. In such a case, since the rigidity of each portion in the absorbent body material depends on the densely gathered state of the absorbent fiber accumulated in that portion, the interspersed section in which an empty layer is formed has less rigidity than the area around the interspersed section. Therefore, it is easier to fold the absorbent article so as to form the fold line.

Also, the absorbent article may have a longitudinal direction; a lateral direction, and a thickness direction; the fold line may be aligned with the lateral direction of the absorbent article; a border between a center section of the absorbent article in the longitudinal direction of the absorbent article and an end section of the absorbent article in the longitudinal direction of the absorbent article may be at a position where the fold line is formed; and a channel section may be formed on the skin face side of the absorbent body material, the channel section extending from a portion positioned in the center section of the absorbent article in the longitudinal direction of the absorbent article to the end section of the absorbent article in the longitudinal direction of the absorbent article. With such an absorbent article, it becomes easy to fold the absorbent article for wrapping, and also it becomes easy to bend the absorbent article in the longitudinal direction thereof when the absorbent article is worn.

Absorbent Article According to Present Embodiment

Overall Configuration of Absorbent Article

Figure 2:
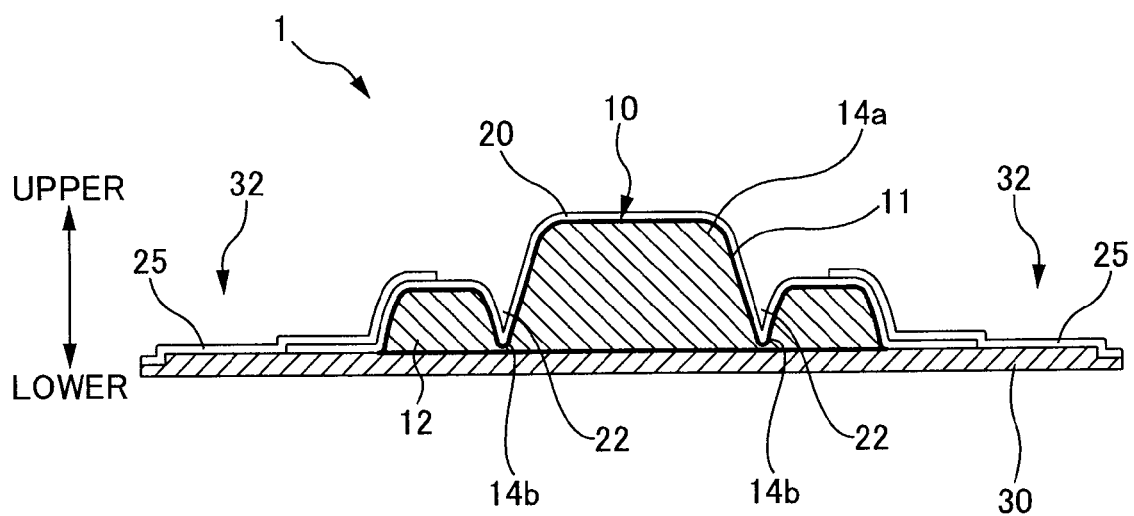
FIG. 2 is a cross sectional view taking along line A-A' in FIG. 1.

First, as an example absorbent article of the present embodiment, using a sanitary napkin as an example (referred to below as an "absorbent article 1"), an example configuration of the absorbent article 1 will be described using FIGS. 1 and 2. FIG. 1 is a schematic plan view of the absorbent article 1, in which a longitudinal direction and a lateral direction (referred to below also as a "width direction") of the absorbent article 1 are indicated with arrows. FIG. 2 shows cross section A-A' in FIG. 1, in which a vertical direction (referred to below also as a "thickness direction") is indicated with an arrow. In the following description, among surfaces positioned in the thickness direction of the absorbent article 1, a face that contacts a body of a wearer is referred to as a skin face, and a face that contacts an undergarment is referred to as an opposite face. Also, in the longitudinal direction of the absorbent article 1, an end that is positioned on a front side (an abdomen side) of the wearer when worn is referred to as a front end, and an end that is positioned on a rear side (a buttocks side) is referred to as a rear end. FIG. 1 shows the skin face side of the absorbent article 1.

The absorbent article 1, as shown in FIG. 1, has an outer shape that is elongated in a certain direction, and is approximately gourd-shaped. This absorbent article 1 includes an absorbent body 10 having a substantially rectangular shape for absorbing moisture such as menstrual blood or perspiration, a fluid-permeable surface sheet 20 that covers a surface of a skin face side of the absorbent body 10, side sheets 25 disposed at both ends in the width direction of the absorbent body 10 on the skin face side of the absorbent body 10, and a back face sheet 30 provided on the opposite face side of the absorbent body 10.

The absorbent article 1 is folded up at predetermined folding line positions (indicated by the double-dotted chained line in FIG. 1) for wrapping. Specifically described, the absorbent article 1 of the present embodiment includes two folding line positions, and is individually wrapped in a state folded in three. That is, the folding line position serves as a position where a fold line, which is formed when the absorbent article 1 has been folded up for individual wrapping, is formed. In the present embodiment, when the absorbent article 1 is folded up, a fold line is formed aligned with the lateral direction of the absorbent article 1. A folding process of the absorbent article 1 will be described later in detail. Also, in the present embodiment, forming positions of the fold lines (i.e. folding line positions) are border lines that divide a front end section, a center section, and a rear end section in the longitudinal direction of the absorbent article 1. That is, in the longitudinal direction of the absorbent article 1, a portion that is in the front end side with respect to the fold line position of the front end side is the front end section, a portion that is in the rear end side with respect to the fold line position of the rear end side is the rear end section, and a portion between the fold line positions at the two locations is the center section.

On the other hand, the absorbent article 1 is worn in a state in which the absorbent article 1 is bent such that a center section in the width direction of the absorbent article 1 is projected. Specifically, the absorbent article 1 is bent in the longitudinal direction of absorbent article 1 for wearing, and is worn with a shape of the absorbent article 1 in the width direction being distorted. Thus, when the absorbent article 1 is worn by the wearer, the center section in the longitudinal direction of the absorbent article 1 contacts the wearer at the groin (around the menstrual blood discharge opening of the wearer), the front end section contacts the wearer from one end section of the groin to the abdomen, and the rear end section contacts the wearer from the other end section of the groin to the buttocks.

As shown in FIG. 1, the absorbent body 10 is attached in the center section in the width direction of the absorbent article 1, and a longitudinal direction of the absorbent body 10 and the longitudinal direction of the absorbent article 1 are aligned with each other. A swelling section 10a swelling toward the skin face side is formed in a portion that is positioned in a center in the longitudinal direction of the absorbent body 10, and positioned in a center in the width direction. The swelling section 10a is formed in an oval shape. When the wearer is wearing the absorbent article 1, conforming to a shape of the groin of the wearer, the swelling section 10a fits closely to the groin via the surface sheet 20. On the other hand, in the absorbent article 1, the end section in the longitudinal direction in an area where the absorbent body 10 is present contacts the abdomen or the buttocks of the wearer. Therefore, the length in the longitudinal direction of the absorbent body 10 is such that in the absorbent article 1, regions where both end sections in the longitudinal direction of the absorbent body 10 are present contact the abdomen and the buttocks of the wearer. Thus, the absorbent body 10 is included in the absorbent article 1 in a state straddling the aforementioned forming positions of the fold lines (i.e., the folding line positions of the absorbent article 1). The forming positions of the fold lines serve as borders dividing the center section and the end sections in the longitudinal direction of the absorbent body 10.

Also, the absorbent body 10 according to the present embodiment is configured from, for example, a thin paper 11 such as tissue paper and an absorbent body material 12. The absorbent body material 12 has a function to absorb and hold fluid that has penetrated from the surface sheet 20 side to the absorbent body 10 side, and has approximately the same outer dimensions as the absorbent body 10. The thin paper 11 is one example of a covering member, and is a sheet that covers so as to surround the absorbent body material 12. Also, in order to integrate the thin paper 11 and the absorbent body material 12 covered by the thin paper 11, a predetermined portion of the absorbent body 10 is compressed, so that embossing (below, also referred to as absorbent body embossing) is formed in that portion. The absorbent body 10 will be described in detail below.

The surface sheet 20 is a fluid-permeable sheet member. This surface sheet 20 is formed from woven or nonwoven fabric or a perforated plastic sheet or the like that has been formed from natural fiber such as pulp or cotton, cellulose fiber such as rayon, or a thermoplastic hydrophobic fiber such as polyethylene or polypropylene. Also, the surface sheet 20 is included in the center section in the width direction of the absorbent article 1, on the skin face side of the absorbent article 1 (that is, one end face in the thickness direction of the absorbent article 1), has a width slightly wider than the absorbent body 10 in the width direction and about the same length as the back face sheet 30 in the longitudinal direction, and covers the entire surface of the absorbent body 10.

The back face sheet 30 is an example of an absorbent article main unit, and is a fluid-impermeable sheet member. The back face sheet 30 is formed from a film sheet constituted of resin of polyethylene, polypropylene, or the like, and the absorbent body 10 is provided on a surface of the back face sheet 30 on the skin face side. Since the absorbent body material 12 is included in the absorbent body 10, the absorbent body material 12 is provided on the surface of the back face sheet 30 on the skin face side. That is, of the skin face side and opposite face side of the absorbent article 1, the skin face side corresponds to a side in which the absorbent body material 12 is provided in the absorbent article 1.

The back face sheet 30, on the side of the opposite face of the absorbent article 1 (that is, a face of the other end of the absorbent article 1 in the thickness direction), is formed sufficiently wider than the absorbent body 10, and an entire circumference of an outer edge section thereof is positioned to the outside of the outer edge section of the absorbent body 10. Also, on both sides in the width direction, holding sections 32 are formed protruding to the outside in the width direction. When the absorbent article 1 is worn, the holding sections 32 are, in a state folded back to the opposite face side, fixed to the undergarment. Also, the back face sheet 30 according to the present embodiment is a fluid-impermeable sheet foamed from thermoplastic fiber of polyethylene, polypropylene, or the like, but it is also possible to use a sheet member in which thin paper, nonwoven fabric, or the like has been layered and that includes a thermoplastic and fluid-impermeable sheet. In a surface of the back face sheet 30 positioned on the opposite face side, a releasing sheet 34 is included via an adhesive 35 in an area where the absorbent body 10 is present on the skin face side and areas where the holding sections 32 are present (see FIGS. 7 and 8). A parting agent is applied to the releasing sheet 34, and the releasing sheet can easily be peeled away from the adhesive 35. When the absorbent article 1 is worn, in a state in which the releasing sheet 34 has been peeled away, the surface (more precisely, the aforementioned area where the absorbent body 10 is present on the skin face side) of the opposite face side of the back face sheet 30 is attached to the inside of an undergarment by the adhesive 35 interposed between the back face sheet 30 and the undergarment. Further, the holding sections 32 are folded back to the outside, so the surface on the opposite side of the back face sheet 30 (more precisely, the aforementioned areas where the holding sections 32 are present) is attached to an outer face of the undergarment by the adhesive 35. When the back face sheet 30 is attached to the undergarment, the absorbent article 1 is positioned and held by the undergarment.

The side sheets 25 are sheets that overlap a portion of the surface sheet 20 (more precisely, both end sections in the width direction of the surface sheet 20), and are included on the skin face side of the absorbent article 1 in end sections in the width direction of the absorbent article 1. The side sheets 25 are formed from an appropriate nonwoven fabric, such as air-through nonwoven fabric or spun-bonded nonwoven fabric formed with a synthetic resin fiber, or nonwoven fabric made up of spun-bonded/melted-blown/spun-bonded layers.

In the absorbent article 1 configured as described above, the skin face of the absorbent body 10 and the surface sheet 20 are joined with hot melt adhesive. Furthermore, on the skin face of the absorbent body 10 and the surface sheet 20, a channel embossing process of pressing in the thickness direction using a high-temperature pressing member is performed. By the channel embossing process, the absorbent body 10 and the surface sheet 20 are compressed as a single body, and are thereby more strongly joined. Also, a deep channel section 22 as shown in FIG. 1 is formed in the portion where the channel embossing process is performed. This deep channel section 22 extends to the absorbent body material 12 included in the absorbent body 10, as shown in FIG. 2. In other words, a channel section 14b having approximately the same shape as the deep channel section 22 is formed in the absorbent body material 12 as well, on one end side in the thickness direction of the absorbent body material 12 (a skin face side of the absorbent body material 12).

As shown in FIG. 1, the deep channel section 22 according to the present embodiment is configured from a portion that surrounds a front end side and a rear end side of the swelling section 10a, and a portion extended from the front end section to the rear end section of the absorbent article 1 in the longitudinal direction on both sides of the swelling section 10a. Further, in the present embodiment, inside the deep channel section 22, along the deep channel section 22, a shallow bottom section and a deep bottom section whose channel depths differ from each other are alternately disposed. On the other hand, as stated above, since the channel section 14b formed in the absorbent body material 12 has approximately the same shape as the deep channel section 22, the channel section 14b extends from a portion positioned in the front end section to a portion positioned in the rear end section of the absorbent article 1.

Due to this sort of deep channel section 22 being formed (in other words, due to the channel section 14b being formed in the absorbent body material 12), when the absorbent article 1 has been bent along the longitudinal direction of the absorbent article 1 for wearing, both end sections of the absorbent article 1 in the longitudinal direction follow the center section in the longitudinal direction and are easily bent. That is, the deep channel section 22 is a bend-inducing section (a so-called hinge section) that facilitates three-dimensional bending in order to bring the portion that corresponds to the aforementioned swelling section 10a into closer contact with the body when the absorbent article 1 is worn. Further, the deep channel section 22 also has a function to, when menstrual blood or the like has flowed into the deep channel section 22, suppress scattering of the menstrual blood or the like by facilitating penetration to a location that has been compressed with high density (i.e., a deep bottom section). Also note that in the present embodiment, the shallow bottom section and the deep bottom section are alternately disposed in the deep channel section 22, but this is not a limitation; for example, the channel depth in the deep channel section 22 may be uniform.

Further, the back face sheet 30 is joined with hot melt adhesive to each opposite face side of the absorbent body 10 and the surface sheet 20. Also, the side sheet 25 is joined with hot melt adhesive to the skin face side of the absorbent body 10, from a position slightly overlapping both side sections of the absorbent body 10 to the back face sheet 30. At positions where the back face sheet 30, the absorbent body 10, the surface sheet 20, and the side sheet 25 overlap, an embossing process is performed with pressing member heated to a low temperature, thus more strongly joining the absorbent body 10, the surface sheet 20, the side sheet 25, and the back face sheet 30. Furthermore, a round sealing process is performed in which the outer edge section of the absorbent article 1 is hot melt bonded at a low temperature. As described above, the absorbent body 10, the surface sheet 20, the side sheet 25, and the back face sheet 30 are joined by an embossing process, hot melt adhesive, or the like.

Structure of Absorbent Body Material

Figure 3:
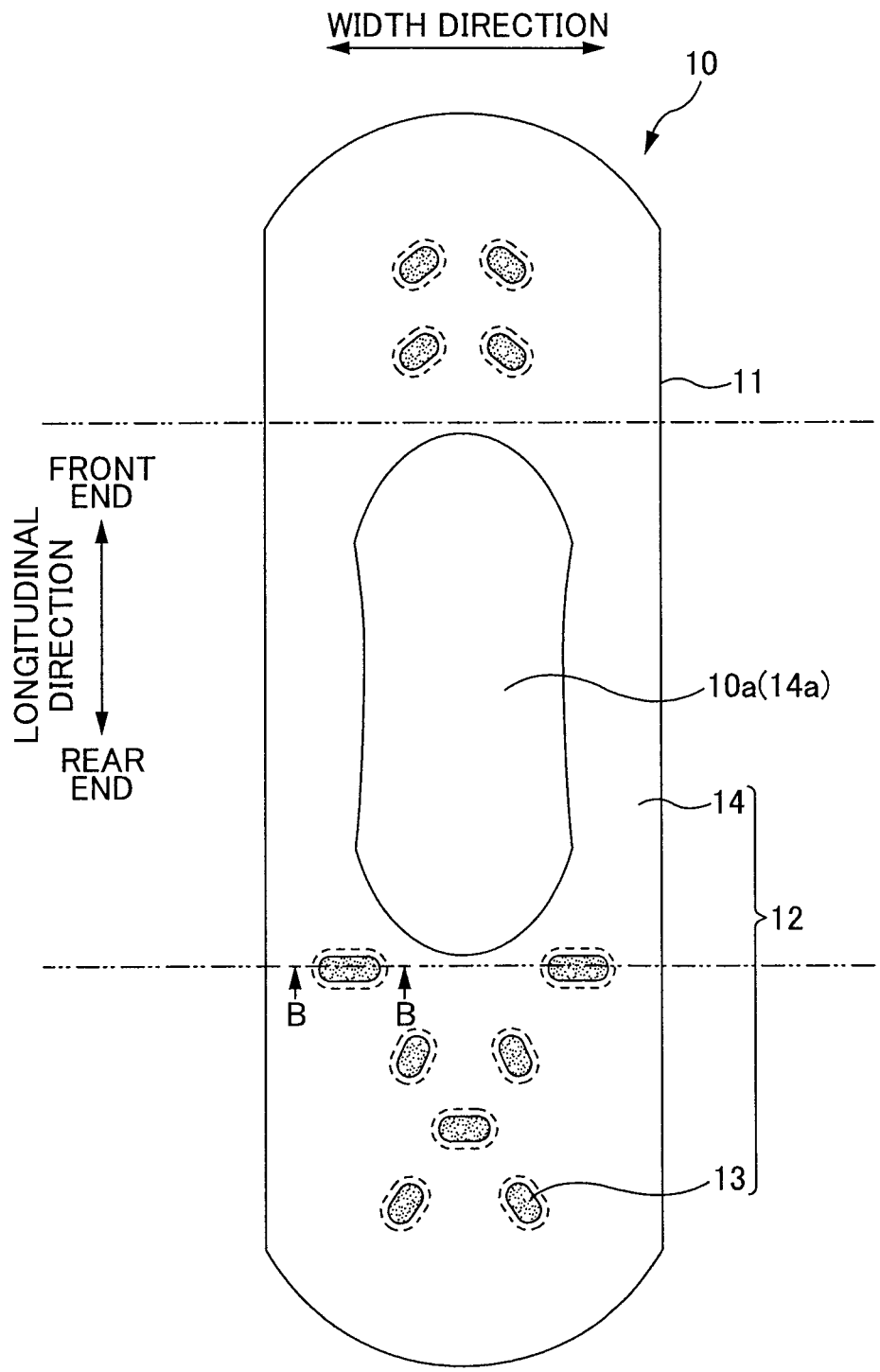
FIG. 3 is a schematic plan view of an absorbent body 10.
Figure 4:
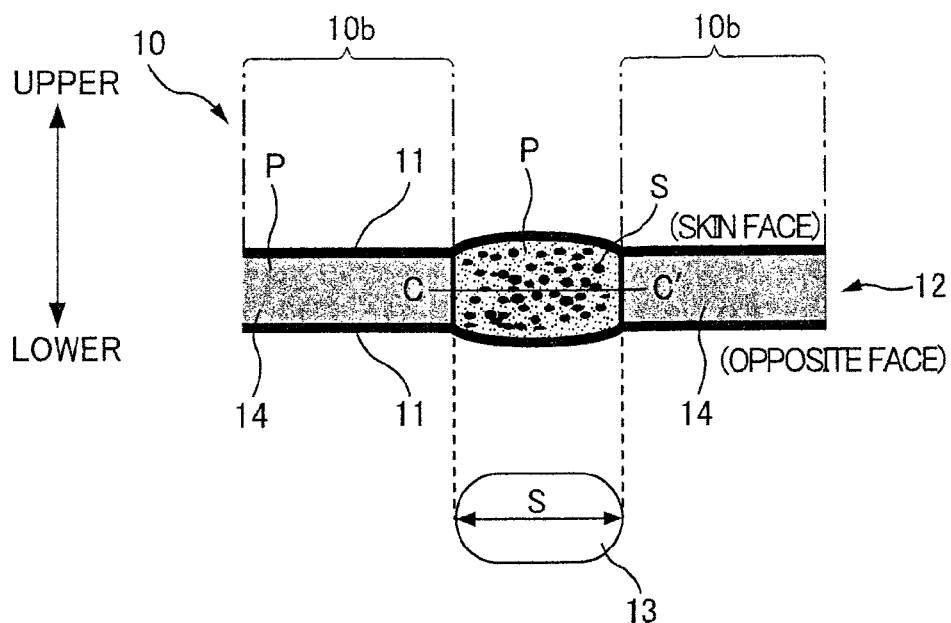
FIG. 4 is a diagram showing a cross-sectional structure of an interspersed section 13.

Next is a description of the structure of the absorbent body 10 of the present embodiment, using aforementioned FIGS. 1, 3, and 4. FIG. 3 is a schematic plan view of the absorbent body 10, and shows the skin face side of the absorbent body 10. In the figure, the longitudinal direction and the width direction of the absorbent body 10 are indicated with arrows. Note that in the absorbent body 10, an indentation that corresponds to the deep channel section 22 is formed at the portion where the stated deep channel section 22 is formed (i.e., the portion where the channel embossing process is performed). However, for the sake of description, such indentation is not shown in FIG. 3. FIG. 4 is a diagram showing a cross-sectional structure of an interspersed section 13, and shows cross section B-B' (upper diagram) in FIG. 3, and a cross-sectional shape (lower diagram) of the interspersed section 13. In the upper diagram in FIG. 4, the vertical direction (i.e., the thickness direction of the absorbent body 10) is indicated with an arrow.

The absorbent body 10 is an approximately sheet-shaped member, and as described above, is configured from the thin paper 11 and the absorbent body material 12.

The absorbent body material 12 is provided in the absorbent article 1 in a state straddling the folding line positions of the absorbent article 1, similarly to the absorbent body 10. The forming positions of the fold lines serve as borders dividing a center section and end sections in the longitudinal direction of the absorbent body material 12. Accordingly, in the absorbent body material 12, positions corresponding to the folding line positions of the absorbent article 1 (indicated by the double-dotted chained line in FIG. 3) serve as positions at which the center section and the end sections are divided in the longitudinal direction of the absorbent body material 12. Also, in a portion that is positioned in the center in the longitudinal direction of the absorbent body material 12, and positioned in the center in the width direction, a thick wall section 14a is formed that is thicker than other portions and is a portion that corresponds to the swelling section 10a of the absorbent body 10.

The absorbent body material 12 is configured from pulp fiber (pulp that has been pulverized into a fibrous state) as an example of absorbent fiber, and granular super absorbent polymer (below, abbreviated as SAP) as an example of super absorbent resin. The pulp fiber is accumulated in sheet-like form, and the SAP is densely gathered in portions of the absorbent body material 12. In an absorbent article 1 including this sort of absorbent body material 12, moisture on the skin face side of the absorbent article 1 is absorbed by the pulp fiber accumulated within the absorbent body material 12, and penetrates into the absorbent body material 12. The moisture that has penetrated into the absorbent body material 12 is dispersed within the absorbent body material 12, and ultimately is collected by SAP that is densely gathered in portions of the absorbent body material 12. It is in the nature of SAP to swell when moisture is collected therein, and SAP is a material with excellent moisture-absorbing properties. Included in the absorbent body material 12 may be, other than pulp fiber, cellulose such as cotton, regenerated cellulose such as rayon or fibril rayon, semisynthetic cellulose such as acetate or triacetate, a fibrous polymer, a thermoplastic hydrophobic fiber, or the like.

The thin paper 11 is fluid-permeable, and is a sheet with perforations that are smaller than the grains of SAP, and therefore has a function to prevent SAP from leaking outside of the thin paper 11. Furthermore, the thin paper 11 has a function to prevent the accumulated pulverized pulp from dropping outside of the thin paper 11. Note that the covering member is not limited to the thin paper 11 such as tissue; it is also possible to use a woven or nonwoven fabric formed from, for example, cellulose such as cotton, regenerated cellulose such as rayon or fibril rayon, semisynthetic cellulose such as acetate or triacetate, a fibrous polymer, or thermoplastic hydrophobic chemical fiber or the like.

Below, the configuration of the absorbent body material 12 of the present embodiment will be specifically described with reference to FIGS. 3 and 4. As shown in FIG. 3, the absorbent body material 12 includes the interspersed sections 13 that are interspersed and the continuous section 14 that is continuous around the interspersed sections 13. The interspersed sections 13 are areas where SAP is densely gathered, and are formed in an oval shape when the absorbent body material 12 is viewed from the skin face side, as shown in the lower diagram in FIG. 4. Specifically, the cross section of the interspersed section 13 that is taken along an orthogonal plane orthogonal to the thickness direction of the absorbent body material 12 (plane C-C' shown in the upper diagram in FIG. 4) has an oval shape.

Also, as shown in the upper diagram in FIG. 4, in the interspersed sections 13 of the present embodiment, SAP (indicated by letter S in FIG. 4, etc.) and pulp fiber (indicated by letter P in FIG. 4, etc.) are intermingled. The interspersed sections 13 are mainly interspersed in the end sections in the longitudinal direction of the absorbent body material 12, and also, as shown in FIG. 3, of the front end section and the rear end section, more of the interspersed sections 13 are present in the rear end section. Note that naturally, the shape and disposition of the interspersed section 13 when the absorbent body material 12 is viewed from the skin face is similar to those when the absorbent article 1 is viewed from the skin face. On the other hand, pulp fiber is approximately uniformly densely gathered in the continuous section 14. Also, the aforementioned absorbent body embossing is formed in a portion (below, a surrounding section 10b) that is in of the absorbent body 10 and that corresponds to an outer circumferential edge of each interspersed section 13.

The interspersed sections 13 according to the present embodiment will now be described in more detail. The densely gathered state of pulp fiber in the interspersed sections 13 is less dense than the densely gathered state in the continuous section 14. Here, because the same pulp fiber is densely gathered in the interspersed sections 13 and the continuous section 14, the densely gathered state of pulp fiber means the weight of pulp fiber included per unit volume (referred to below as "pulp density"). Also, in the present embodiment, because the respective pulp densities are approximately uniform in the interspersed sections 13 and the continuous section 14 in the thickness direction of the absorbent body material 12, the densely gathered state of pulp fiber is indicated by the weight of pulp fiber included per unit area in a plane defined by the longitudinal direction and the width direction of the absorbent body material 12 (below, weight). Accordingly, the weight of pulp fiber in the interspersed sections 13 is less than the weight in the continuous section 14. Also, because absorbent body embossing is formed in the surrounding section 10b, the surrounding section 10b is in a compressed state. In other words, because the absorbent body embossing is formed while avoiding positions that correspond to each of the interspersed sections 13, as shown in the upper diagram in FIG. 4, each of the interspersed sections 13 is thicker than portions that correspond to the surrounding sections 10b in the absorbent body material 12. Regarding the interspersed sections 13 configured in this manner, its rigidity, which depends on the densely gathered state of the pulp fiber, is less than the rigidity of the continuous section 14, and cushioning of those interspersed sections is higher than the cushioning of the continuous section 14. Thus, when the absorbent article 1 is being worn, portions that correspond to the interspersed sections 13 feel soft to the skin of the wearer.

Further, as shown in FIG. 3, among the interspersed sections 13, interspersed sections 13 are present that are disposed at a portion corresponding to the folding line position in the absorbent article 1 (specifically, the folding line position on the rear end side). In other words, at least one (two, in the present embodiment) interspersed section 13 is present that overlaps the fold line formed when the absorbent article 1 has been folded up for individual wrapping (specifically, the fold line formed in the further rear end side in the absorbent article 1). When viewed from the skin face side of the absorbent body material 12, a longitudinal direction of the interspersed section 13 overlapping the fold line (a direction indicated by reference symbol S in the lower diagram in FIG. 4, and a major axis direction of the cross section of the interspersed section 13) is aligned with a lateral direction of the absorbent body material 12; therefore, the longitudinal direction of the interspersed section 13 is aligned with the lateral direction of the absorbent article 1. In other words, in the present embodiment, some interspersed sections 13 are present that overlap the fold line in a state in which the longitudinal direction of such interspersed sections 13 is aligned with the fold line formed in the further rear end side when the absorbent article 1 is viewed from the skin face side. In the following description, the longitudinal direction and a lateral direction of the interspersed section 13 when the absorbent body 10 is viewed from the skin face are simply referred to as the longitudinal direction and lateral direction of the interspersed section 13.

On the other hand, because SAP is densely gathered in the interspersed sections 13, the occupied volume ratio of SAP in each of the interspersed sections 13 is greater than the occupied volume ratio around each of the interspersed sections. Here, the occupied volume ratio of SAP in each of the interspersed sections 13 refers to a ratio of the total volume of SAP disposed in each of the interspersed sections 13 with respect to the volume of each of the interspersed sections 13. Similarly, the occupied volume ratio of SAP in an area around each of the interspersed sections 13, that is, the continuous section 14, refers to the ratio of the total volume of SAP disposed in the continuous section 14 with respect to the total volume of the continuous section 14. Also, SAP in the interspersed section 13 is dispersed within the interspersed section 13, as shown in the upper diagram in FIG. 4.

Method for Producing Absorbent Article

Figure 5:
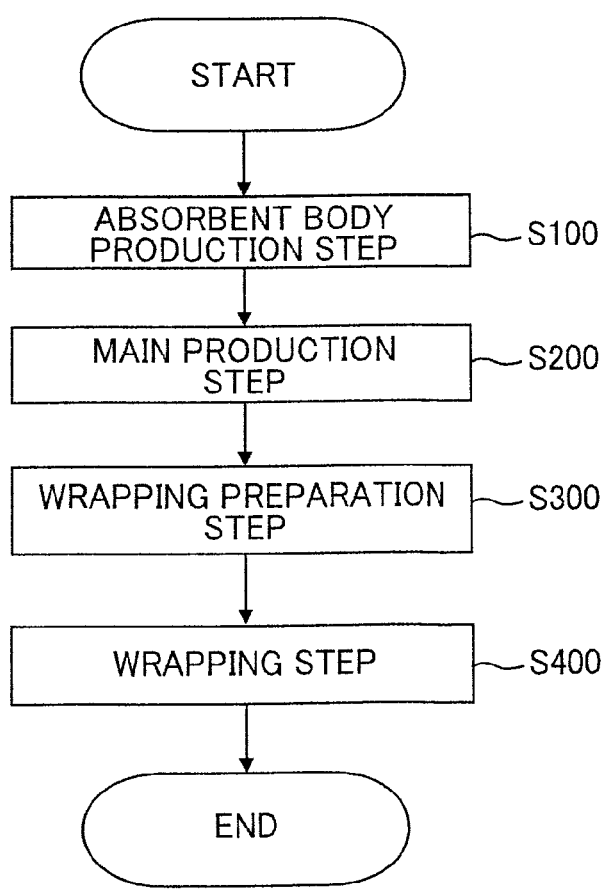
FIG. 5 is a flowchart showing a production flow of the absorbent article 1.

Next is a description of the method for producing the absorbent article 1 of the present embodiment, using FIG. 5. FIG. 5 shows a production flow of the absorbent article 1. The method for producing the absorbent article 1 includes an absorbent body production step S100 of producing the absorbent body 10; a main production step S200 of producing the absorbent article 1 using the absorbent body 10 produced in the absorbent body production step S100, the surface sheet 20, the side sheet 25, and the back face sheet 30; a wrapping preparation step S300 of preparing the absorbent article 1 for wrapping; and a wrapping step S400 of wrapping the absorbent article 1. In the present embodiment, the above steps are executed while materials and products of the absorbent article 1 are transported by a transport apparatus such as a conveyer. Following is a description of each step.

Absorbent Body Production Step

Figure 6:
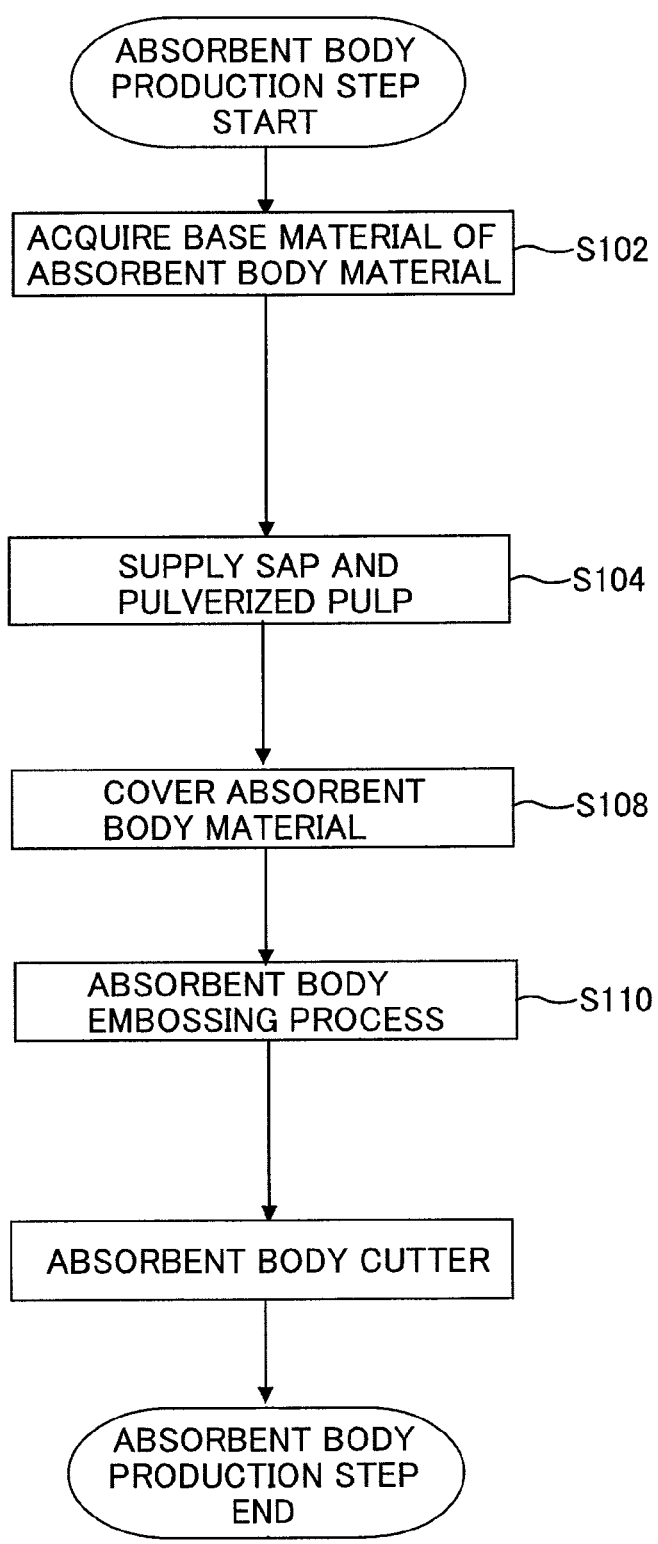
FIG. 6 is an explanatory diagram of an absorbent body production step S100.
Figure 6:
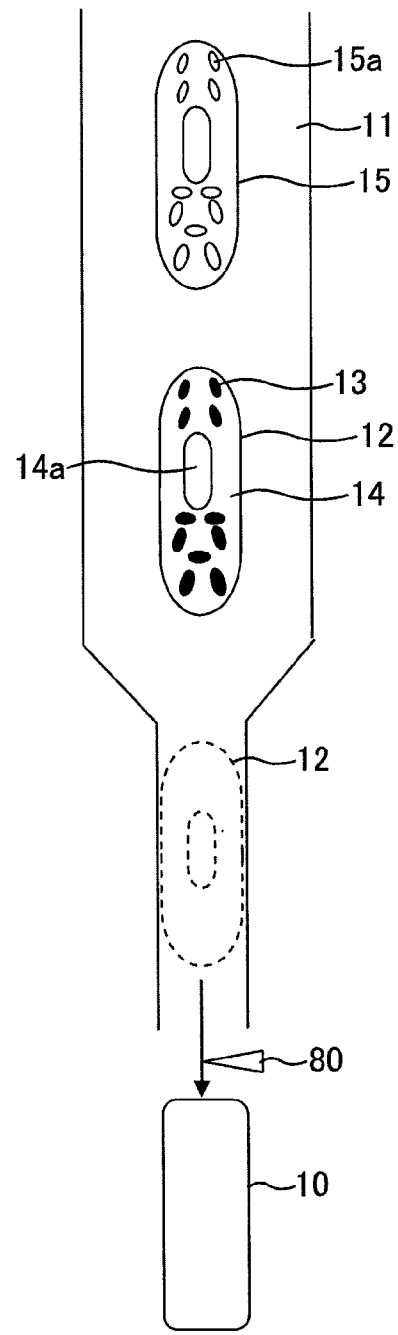

First, the absorbent body production step S100 will be described using FIG. 6. FIG. 6 illustrates the absorbent body production step S100, and includes a flowchart of the absorbent body production step S100 (left of FIG. 6), and an image of the absorbent body 10 that is being produced (right of FIG. 6). The right side of FIG. 6 schematically shows how material of the absorbent body 10 and the absorbent body 10 in the course of production are placed on a transport apparatus such as a conveyor and move.

The absorbent body production step S100 starts from Step S102 of acquiring the base material 15 of the absorbent body material. The base material 15 is acquired by performing a process of accumulating pulp fiber within a mold frame. Also, as shown in FIG. 6, in the base material 15 of absorbent body material, hole sections 15a are provided in portions where the interspersed sections 13 are formed. The hole section 15a is formed in an oval shape when the base material 15 is viewed from above, and each hole section 15a penetrates the base material 15 from one end to the other end in a thickness direction of the base material 15. The hole sections 15a are mainly interspersed in end sections in a longitudinal direction of the base material 15. Furthermore, among hole sections 15a according to the present embodiment, at least one hole section 15a is present at a position where the fold line is formed when the absorbent article 1 has been completed and individually wrapped (i.e., a position corresponding to the folding line position in the absorbent article 1). When the base material 15 is viewed from above, a longitudinal direction of the hole section 15a is aligned with a lateral direction of the base material 15.

When the above base material 15 is acquired, the base material 15 is transported in a predetermined transport direction by a transport apparatus. At this time, the continuous strip-like thin paper 11 is supplied in advance on a face provided in the transport apparatus for placing the base material 15 (below, a placement face). In a state in which the base material 15 has been placed on the thin paper 11, the base material 15 is transported along with the thin paper 11 in the transport direction. Note that transport is performed in a state in which, of surfaces of the base material 15 in the thickness direction, the surface that comes to the skin face side at the point of completion as an absorbent article 1 is facing downward (the transport apparatus side). Further, a suction mechanism is provided in the transport apparatus according to the present embodiment, and the base material 15 and the thin paper 11 are transported while being drawn to the transport apparatus side with the suction force of this suction mechanism.

Next, to the base material 15 in the transport state, SAP and pulp fiber are supplied into the hole sections 15a provided in the base material 15 (S104). In the present embodiment, SAP is supplied from above the base material 15 by a not-shown SAP supply mechanism. At this time, as described above, the base material 15 is drawn to the transport apparatus side by the suction mechanism. Because a suction resistance in the hole sections 15a is sufficiently smaller than a suction resistance in portions of the base material 15 other than the hole sections, SAP supplied from the SAP supply mechanism is sucked into the hole sections 15a. That is, SAP is concentratedly supplied to the hole sections 15a, and densely gathered within the hole sections 15a. As a result, SAP is supplied such that the occupied volume ratio of SAP in the hole sections 15a is higher than the occupied volume ratio of SAP in portions of the base material 15 other than the hole sections 15a. Also, in the present embodiment, an amount of SAP supplied to each hole section 15a is adjusted such that the filling ratio of SAP in each hole section 15a is the same between hole sections 15a.

Also, in the present embodiment, along with supplying SAP into each hole section 15a with the suction force of the suction mechanism, using the suction force, part of the accumulated pulp fiber is removed from portions of the base material 15 that are adjacent to each of the hole sections 15a (below, adjacent sections). The removed pulp fiber is supplied to the hole sections 15a and is accumulated within the hole sections 15a. Thus, a suction pressure of the suction apparatus is adjusted such that pulp fiber is removed from the adjacent sections and supplied into the hole sections 15a. As a result, pulp fiber and SAP are mixed within each hole section 15a, and ultimately the absorbent body material 12 is formed from the base material 15. That is, the aforementioned interspersed sections 13 are formed in the hole sections 15a, and the portions of the base material 15 other than the hole sections 15a become the continuous section 14. Also, by adjusting the suction pressure of the suction apparatus, it becomes possible to also adjust the amount of pulp fiber removal. In the present embodiment, the amount of removal is adjusted such that when the interspersed sections 13 have been formed in the hole sections 15a, the weight of pulp fiber in the interspersed sections 13 is less than the weight in the continuous section 14.

When the absorbent body material 12 has been formed, as shown in FIG. 6, the thin paper 11 interposed between the absorbent body material 12 and the transport apparatus is bent so as to surround the absorbent body material 12, thus covering the absorbent body material 12 (S108). Afterward, in order to integrate the thin paper 11 and the absorbent body material 12, a predetermined portion of the absorbent body material 12 that is in a state covered by the thin paper 11 is compressed, thus executing an absorbent body embossing process that forms absorbent body embossing at that predetermined portion (S110). In the present embodiment, the predetermined portion is, as described above, a portion corresponding to the surrounding section 10b that is the continuous section 14 and surrounds the interspersed sections 13. The absorbent body embossing process is performed by passing between two rollers (not shown) that vertically oppose each other. For example, a protrusion of a predetermined shape is formed in the lower roller on a portion that contacts a region where the absorbent body embossing is formed when the absorbent body material 12 has been transported (that is, a region that corresponds to the surrounding section 10b), and a surface of the opposing upper roller is formed flat. Due to the absorbent body material 12 surrounded by the thin paper 11 passing between those two rollers, the protrusion compresses both the thin paper 11 and the absorbent body material 12. The thin paper 11 and the absorbent body material 12 are compressed by the protrusion, and become a single body due to the formation of a plurality of absorbent body embossings. Also, in the present embodiment, because absorbent body embossing is formed in the region that corresponds to the surrounding section 10b, pulp fiber accumulated in the region that corresponds to the surrounding section 10b is compressed, as shown in the upper diagram in FIG. 4.

Main Production Step S200

Figure 7:
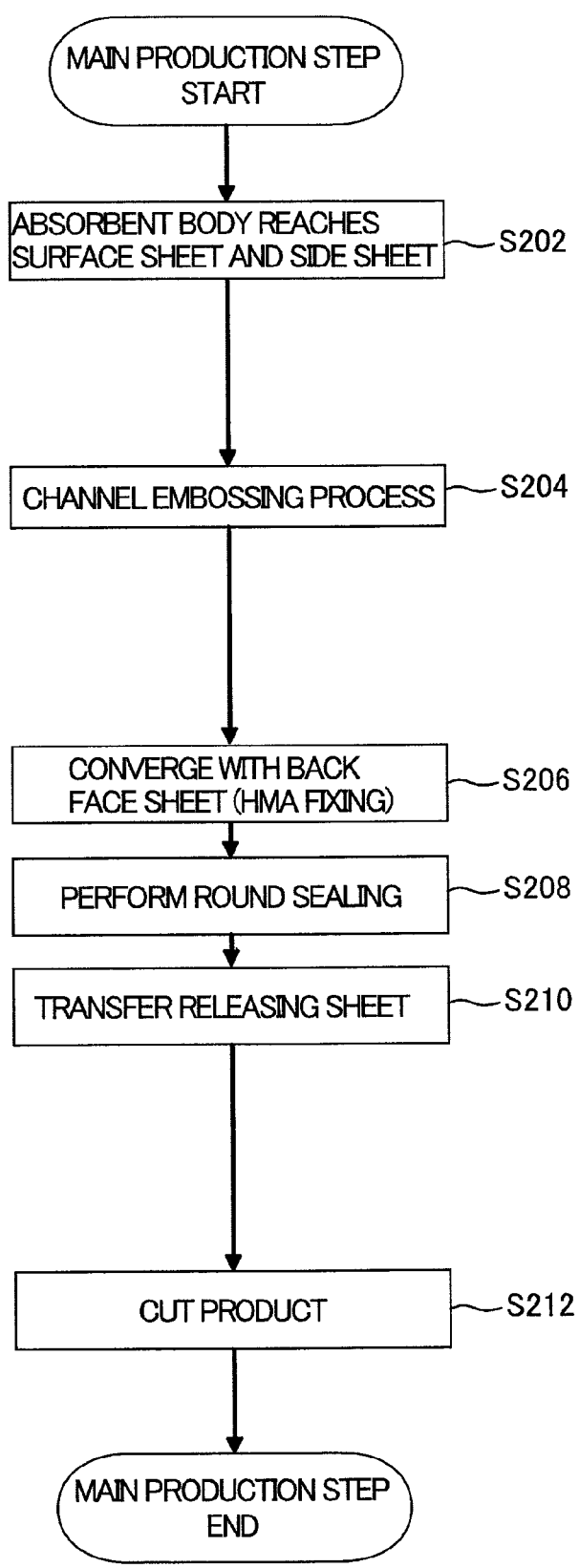
FIG. 7 is an explanatory diagram of a main production step S200.
Figure 7:
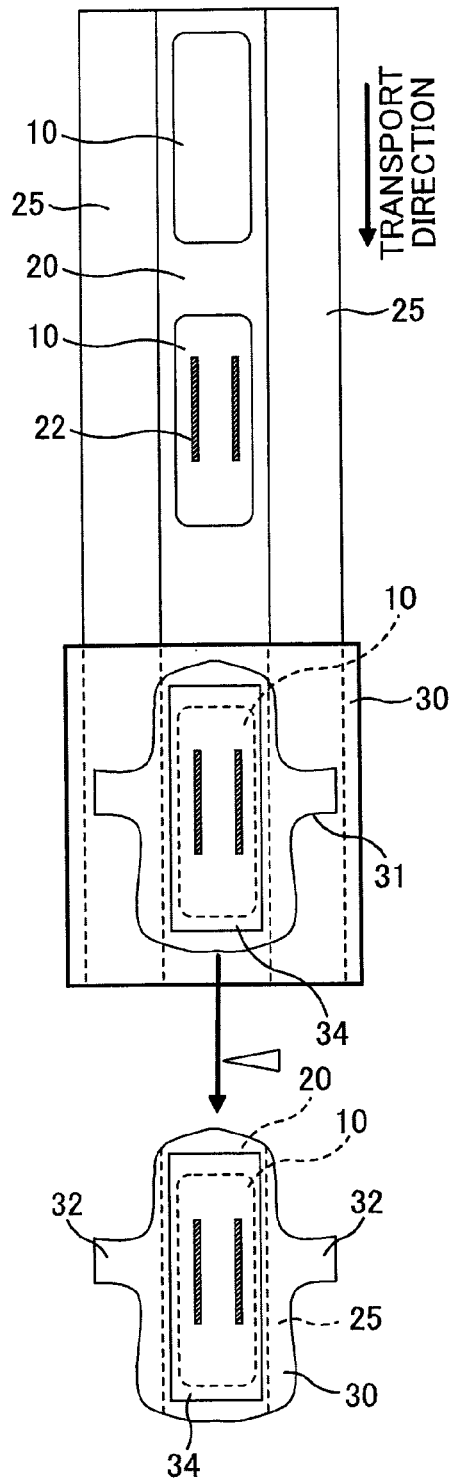

Next, a main production step S200 is described using FIG. 7. FIG. 7 is an explanatory diagram of the main production step S200, and shows a flowchart of the main production step S200 (left diagram) and an image of an article that is being produced (right diagram).

The absorbent body 10 acquired in the absorbent body production step S100 is subsequently transported in the transport direction while being placed on the transport apparatus. Ahead of transport of the absorbent body 10, the surface sheet 20 and the side sheet 25, both of which are strip-shaped and rolled up, are supplied on the placement face of the transport apparatus. At this stage, hot melt adhesive is applied to an upper face of the surface sheet 20. Also in the present embodiment, the surface sheet 20 and side sheet 25 adhere to each other prior to being supplied onto the placement face. Then, when the absorbent body 10 is further transported in the transport direction, the absorbent body 10 converges with the surface sheet 20 and side sheet 25, and is placed on the surface sheet 20, as shown in FIG. 7 (S202). Afterward, the channel embossing process is performed on the absorbent body 10 transported with the surface sheet 20 and side sheet 25 (S204). The deep channel section 22 (see FIG. 1) is formed extending from the front end section to the rear end section in the longitudinal direction by the channel embossing process, so that the absorbent body 10 and the surface sheet 20 are further strongly joined. At this stage, the channel section 14b having approximately the same shape as the deep channel section 22 is formed on the absorbent body material 12 as well. In the present embodiment, inside the deep channel section 22, a shallow bottom section and a deep bottom section whose channel depths differ from each other are formed along the deep channel section 22.

The absorbent body 10, the surface sheet 20, and side sheet 25 are further transported in the transport direction in an integrated state, and afterwards converge with the back face sheet 30 whose width is much wider than a width of the absorbent body 10 (S206). Prior to, converging with the back face sheet 30, hot melt adhesive is applied to upper faces of the absorbent body 10, surface sheet 20, and side sheet 25 (i.e., faces that come to the opposite side), and the back face sheet 30 adheres with the hot melt adhesive to the absorbent body 10, surface sheet 20, and side sheet 25 (hereinafter, the absorbent body 10, surface sheet 20, and side sheet 25 in an accumulated layer state is collectively referred to as an "accumulated layer absorbent body"). That is, as shown in FIG. 7, an upper face of the accumulated layer absorbent body (i.e., the upper faces of the absorbent body 10, surface sheet 20, and side sheet 25) are covered by the back face sheet 30. In other words, the absorbent body 10 is provided on the surface of the back face sheet 30 in the lower side (surface that comes to the skin face side). Also, the embossing process using a pressing member heated to a low temperature is performed on a position where the back face sheet 30, absorbent body 10, surface sheet 20, and side sheet 25 overlap.

Thereafter, a round sealing process is performed (S208) as a step of forming a joining section 31 over an outer shape of the absorbent article 1, that is, the entire circumference of the outer edge in a planer shape of the absorbent article 1. The round sealing process is a process in which a portion that becomes to the outer edge in the planer shape of the absorbent article 1 is heat-pressed and cured, and the joining section 31 is formed by the round sealing process, the joining section 31 matching the outer edge in the planer shape of the absorbent article 1. The joining section 31 is a portion formed by the back face sheet 30, the surface sheet 20, and the side sheet 25 being joined by the round sealing process.

Next, the releasing sheet 34 with hot melt adhesive applied thereto is placed in a middle section in the upper face of the back face sheet 30 (S210). More specifically, the adhesive 35 is not directly applied to the back face sheet 30, but supplied to the back face sheet 30 in a state in which the adhesive 35 is applied to the releasing sheet 34. When the releasing sheet 34 is transferred to the back face sheet 30 and then removed therefrom, the adhesive 35 remains on the back face sheet 30.

After the releasing sheet 34 is transferred, cutting is performed with a product cutter 82 along the outer edge in the planer shape of the absorbent article 1, that is, along the joining section 31 joined by round sealing, thereby generating the absorbent article 1 (S212). Then, a portion positioned outside of the joining section 31 is removed from each of the surface sheet 20, side sheet 25, and back face sheet 30, so that only the absorbent article 1 is transported to the next process. When each of the above steps is completed, the main production step S200 ends.

Wrapping Preparation Step S300

Figure 8:
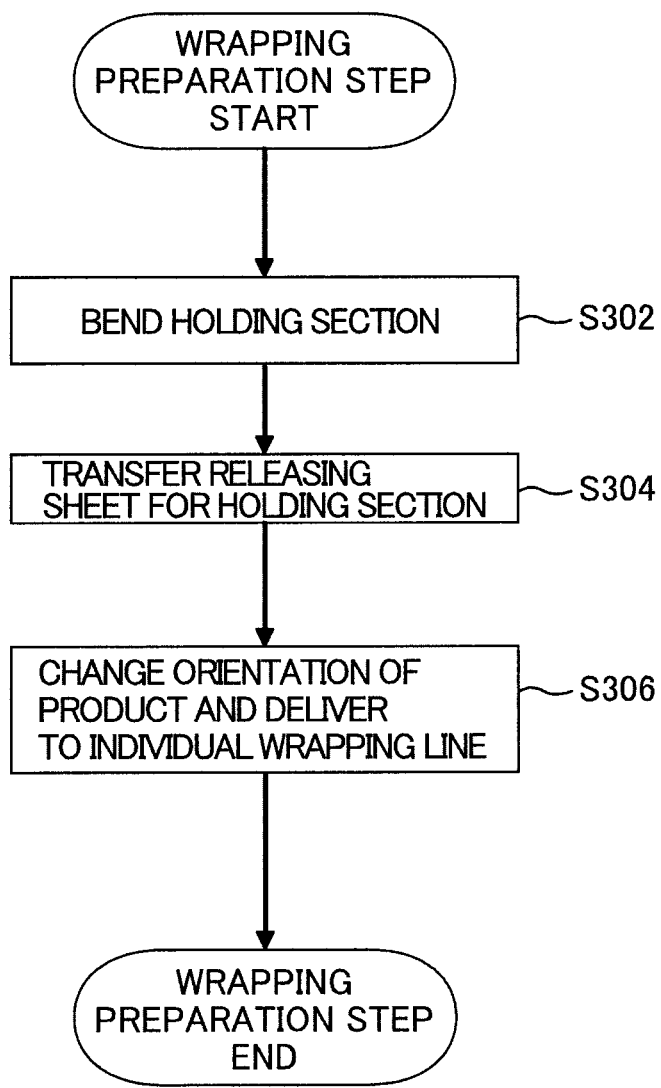
FIG. 8 is an explanatory diagram of a wrapping preparation step S300.
Figure 8:
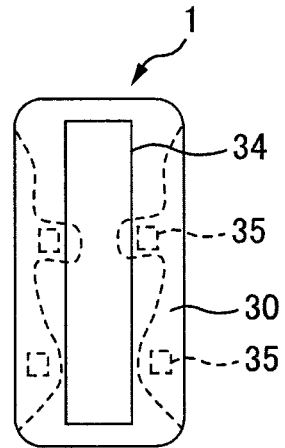
Figure 8:
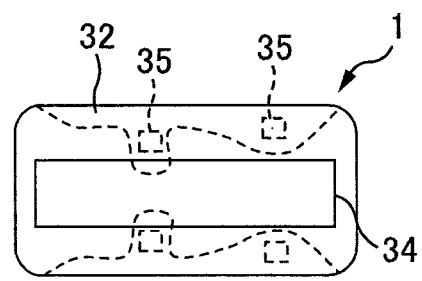

Next, a wrapping preparation step S300 is described using FIG. 8. FIG. 8 is an explanatory diagram of the wrapping preparation step S300, and shows a flowchart of the wrapping preparation step S300 (left diagram) and an image of the absorbent article 1 that is being transformed (right diagram).

Individual absorbent article 1 produced in the main production step S200 is placed on a transport apparatus such as a conveyor, and transported in the transport direction by the transport apparatus. Then, when the absorbent article 1 passes between curved walls (not shown) provided above the transport apparatus, the holding section 32 is guided by such walls and bent toward the surface side (S302). The releasing sheet 34 to which the hot melt adhesives 35 have been applied is placed from the transport apparatus side onto the bent holding section 32 (S304). In this state, the absorbent article 1 is folded up in a substantially rectangular shape, as shown in FIG. 8. The orientation of the absorbent article 1 on which the releasing sheet 34 has been placed is changed such that the longitudinal direction thereof is aligned with a direction orthogonal to the transport direction, and the absorbent article 1 is delivered to the wrapping step S400 (S306). When each of the above steps is completed, the wrapping preparation step S300 ends.

Wrapping Step S400

Figure 9:
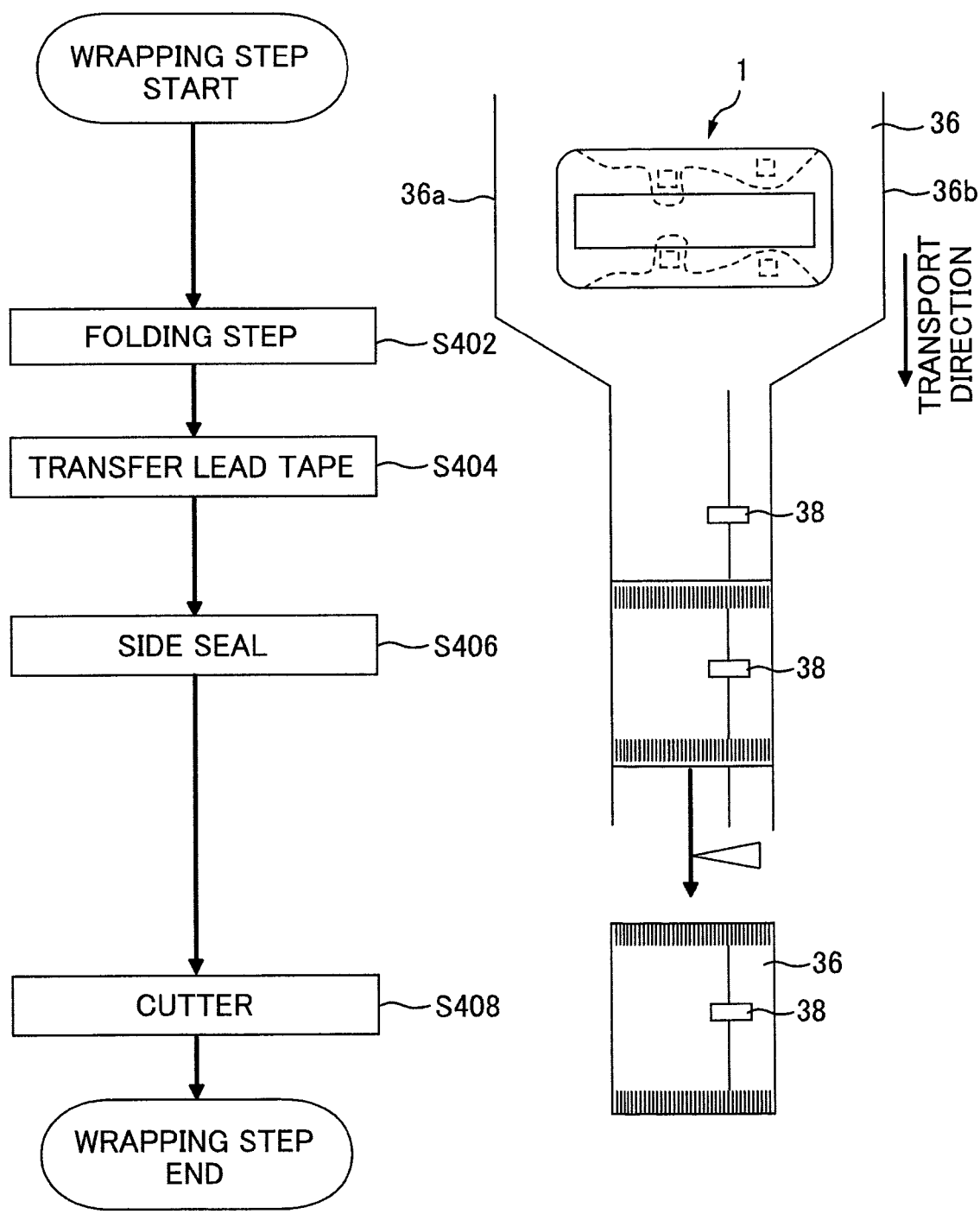
FIG. 9 is an explanatory diagram of a wrapping step S400.

Next, the wrapping step S400 is described using FIG. 9. FIG. 9 is an explanatory diagram of the wrapping step S400, and shows a flowchart of the wrapping step S400 (left diagram) and the image of the absorbent article 1 that is being wrapped (right diagram).

As shown in FIG. 9, the absorbent article 1 that has undergone wrapping preparation is placed on the strip-shaped wrapping sheet 36 supplied on the transport apparatus, with the skin face side of the absorbent article 1 facing upward. A trace amount of hot melt adhesive has been applied to several locations in the wrapping sheet 36 along the longitudinal direction of the absorbent article 1, and thus the back face side of the absorbent article 1 adheres to the wrapping sheet 36 at the several locations. The absorbent article 1 placed on the wrapping sheet 36 is folded in three together with the wrapping sheet 36, while passing between the curved walls (not shown) provided above the transport apparatus (S402). At this stage, some interspersed sections 13 are present on the folding line position on the further rear end side, among the folding line positions of the absorbent article 1 (see FIG. 1). Therefore, when the absorbent article 1 is folded up, the interspersed sections 13 present on the folding line position on the further rear end side overlap the fold line in a state in which the longitudinal direction of the interspersed sections 13 is aligned with the fold line.

Also, when the absorbent article 1 is folded up, the absorbent article 1 is bent together with wrapping sheet 36, and a rear end 36b of the wrapping sheet 36 thereby adheres to the skin face side of the absorbent article 1 with adhesive applied to the rear end 36b of the wrapping sheet 36. On the wrapping sheet 36 on the side of the bent rear end 36b, the absorbent article 1 is bent together with the wrapping sheet 36 on the side of a front end 36a, the front end 36a of the wrapping sheet 36 is overlapped on the outer face of the wrapping sheet 36 that has been already bent and is fixed by the lead tape 38 (S404). After this bending operation, a plurality of the bent absorbent articles 1 are arranged with a spacing interposed therebetween in the transport direction in the tubular wrapping sheet 36, and the absorbent articles 1 are transported. Subsequently, when portions between the adjacent absorbent articles 1 are compression-joined during transportation (a so-called side sealing process), the absorbent articles 1 become connected in an individually wrapped state (S406). Finally, centers of the compression-joined portions between the absorbent articles 1 are cut with a cutter or the like (S408), and thus the individually wrapped absorbent articles 1 are completed. When each of the above steps is completed, the wrapping step S400 ends. When the wrapping step S400 has ended, the production process of the absorbent article 1 of the present embodiment also ends.

Effectiveness of Absorbent Article of Present Embodiment

The absorbent article 1 of the present embodiment is an absorbent article that includes the back face sheet 30 and the absorbent body material 12 provided on the back face sheet 30, and in which a fold line is formed when folded up for individual wrapping. The absorbent article 1 also includes interspersed sections that are the interspersed sections 13 interspersed in the absorbent body material 12, where the densely gathered state of pulp fiber is less dense than the densely gathered state around the interspersed sections 13 and the occupied volume ratio of SAP is greater than the occupied volume ratio of SAP around the interspersed sections 13. Also, when the absorbent article 1 is viewed from the skin face side, the interspersed sections 13 overlap the fold line in a state in which the longitudinal direction of the interspersed section 13 is aligned with the fold line. Such an absorbent article 1 can be easily folded up for individual wrapping.

That is, as described in the Related Art section, there are cases in which areas where SAP is densely gathered (i.e., interspersed sections 13) are interspersed in the absorbent body material 12 including accumulated pulp fiber and SAP. Also, a configuration is conceivable in which the weight of the pulp fiber in the interspersed sections 13 is less than the weight in the vicinity of the interspersed sections 13 (i.e., continuous section 14). With such a configuration, empty space for swelling of SAP is better insured within the interspersed sections 13 than the area around interspersed sections 13. In this case, due to the empty space, even when SAP swells, it is less probable for the interspersed section 13 to bulge in the thickness direction of the absorbent body material 12. As a result, in the absorbent article 1, bulging is suppressed at portions where the interspersed sections 13 are present, so it becomes possible to prevent giving to the wearer a foreign-body sensation caused by the bulging.

On the other hand, when the absorbent article 1 is shipped, the folding process for individual wrapping is performed on the absorbent article 1. The absorbent article 1 is individually wrapped with the fold line being formed therein. With respect to such an individual wrapping process, (for example, the already-stated wrapping step S400), further speeding up of the individual wrapping process has been demanded in order to achieve a fast production line for the absorbent article. In order to speed up the individual wrapping process, it is desirable that the absorbent article 1 is folded more easily at the forming position of the fold line.

The ease of folding the absorbent article 1 depends on the rigidity of each portion of the absorbent body material 12 provided in the absorbent article 1 (especially, the rigidity of portions corresponding to the folding line positions). Also, the rigidity of each portion in the absorbent body material 12 depends on the densely gathered state of the pulp fiber (for example, the weight of pulp fiber) in that portion. Therefore, the interspersed sections 13, where the weight of pulp fiber is less than other portions, have less rigidity than the areas around the interspersed sections 13, namely, the continuous section 14. If a configuration is adopted in which interspersed sections 13 overlap the fold line that is formed when the absorbent article 1 has been folded up for individual wrapping, the absorbent article 1 can be folded up more easily.

Also, when the longitudinal direction of the interspersed section 13 overlaps the fold line as in the present embodiment, compared with cases where the lateral direction of the interspersed section 13 overlaps the fold line, or cases where neither the longitudinal direction nor the lateral direction of the interspersed section 13 overlaps the fold line, it will be easier to fold up the absorbent article 1 so as to form the fold line. As a result, the folding process for individual wrapping of the absorbent article 1 according to the present embodiment is more easily performed.

Furthermore, when the interspersed section 13 of the present embodiment overlaps the fold line, it is easier to fold up the absorbent article 1 for individual wrapping, and also it is easier to bend the absorbent article 1 along the longitudinal direction thereof so as to appropriately bring the absorbent article 1 into close contact to the skin of the wearer, when worn.

Specifically described, a conventional absorbent article (that is, an absorbent article in which the interspersed section 13 does not overlap the fold line, and in particular, an absorbent article in which a portion where pulp fiber is accumulated with high density overlaps the fold line) will be subject to so-called "folding bias" at the folding position once folded up for individual wrapping. That is, when an absorbent article in a folded state is taken out of the wrapping sheet 36 and is opened for wearing, that absorbent article attempts to return to the folded state. It is difficult to attach the absorbent article suffering the folding bias in this manner to the undergarment. In addition, since the absorbent article attempts to return to the folded state even when the absorbent article has been attached to the undergarment, there is a risk that the absorbent article will separate from the undergarment. Further, when the absorbent article with folding bias is worn, the absorbent article will be in a state slightly bent at the folding position, so that a gap occurs between the skin of the wearer and the absorbent article in the vicinity of the folding position. Such a gap gives a foreign-body sensation to the wearer, and sometimes induces leaking of fluid excreted to the skin face side of the absorbent article.

On the other hand, in the absorbent article 1 of the present embodiment, the interspersed section 13 having less rigidity overlaps the fold line, and therefore the absorbent article 1 is easily bent at the folding position. That is, the absorbent article 1 of the present embodiment rarely becomes subject to the folding bias, and rarely attempts to return to the folded state when opened from the folded state. For this reason, it is possible to appropriately attach the absorbent article 1 to the undergarment, and also it is easier to bend the absorbent article 1 along the deep channel section 22, which is a bend-inducing section. In this manner, it also becomes possible to wear the absorbent article 1 closely contacted to the skin of the wearer in an appropriate manner. As a result of the absorbent article 1 closely contacting the skin of the wearer in an appropriate manner, no gap occurs between the skin of the wearer and the absorbent article, thereby preventing giving of a foreign-body sensation due to such a gap and leaking of fluid from such a gap. The above-described effect is more effectively exhibited when the longitudinal direction of the interspersed section 13 is aligned with the fold line.

Other Configurations of Interspersed Section

In the above embodiment, a configuration was described in which in order to prevent partial bulging in the absorbent article 1, the interspersed sections 13 are interspersed in the absorbent body material 12 including pulp fiber and SAP, and in the interspersed sections 13, the weight of pulp fiber is less than the weight of pulp fiber around the interspersed sections 13, and the occupied volume ratio of SAP is greater than the occupied volume ratio of SAP around the interspersed sections 13 (below, referred to as a "first example"). The interspersed sections 13 have, as stated above, less rigidity than the areas around the interspersed sections 13. Therefore, at least one interspersed section 13 overlaps the fold line that is formed when the absorbent article 1 has been folded up, and also as a result of the longitudinal direction of the interspersed section 13 being aligned with the fold line, the absorbent article 1 can be folded up more easily.

Figure 10:
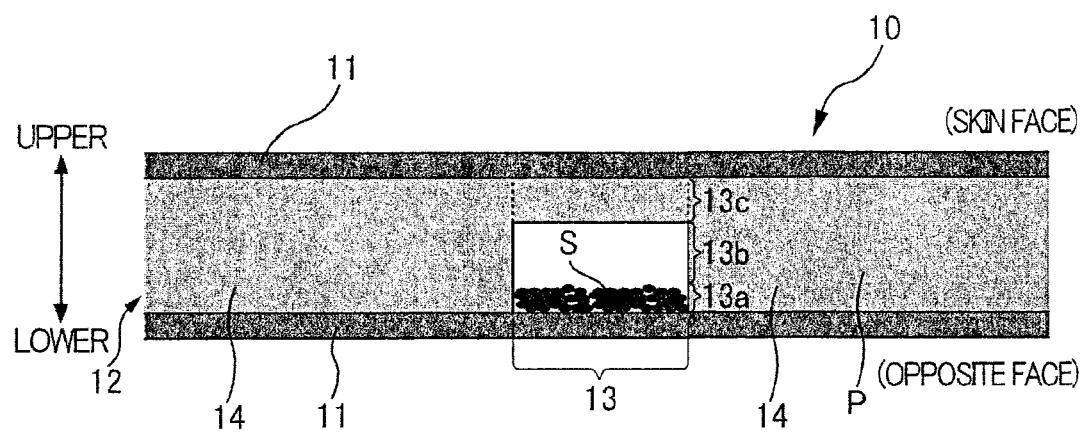
FIG. 10 is a diagram showing a cross-sectional structure of an interspersed section 13 according to a second example.

However, a configuration of the interspersed sections 13 is not limited to the above embodiment; other configurations are also conceivable. Below, another configuration of the interspersed sections 13 (below, referred to as a "second example") will be described using FIG. 10. FIG. 10 is a diagram showing a cross-sectional structure of an interspersed section 13 according to the second example. In FIG. 10, the vertical direction (i.e., the thickness direction of the absorbent body 10) is indicated with an arrow.

As shown in FIG. 10, the interspersed section 13 according to the second example has a three-layer structure in the vertical direction, the structure including a densely gathered layer 13a where SAP is densely gathered, an empty layer 13b, and an accumulated layer 13c where pulp fiber is accumulated. In a state in which the skin face of the absorbent article 1 is above the opposite face, these layers are lined up in the vertical direction from the skin face side in the order of the accumulated layer 13c, the empty layer 13b, then the densely gathered layer 13a. Also the interspersed section 13 according to the second example is formed in an oval shape when the absorbent body material 12 is viewed from the skin face, as in the first example.

On the other hand, in the area around the interspersed section 13 (i.e., the continuous section 14), pulp fiber is accumulated in an approximately uniform densely gathered state. Note that the densely gathered state of pulp fiber in the accumulated layer 13c formed in the interspersed section 13 is approximately the same as the densely gathered state of pulp fiber in the continuous section 14.

In the interspersed section 13 according to the second example having such a configuration, the densely gathered layer 13a of SAP and the empty layer 13b serving as empty space for swelling of SAP are adjacent to each other in the vertical direction, and thus even when SAP has swollen, the increase in volume of SAP due to the swelling can be stopped within the empty layer 13b. As a result, it is possible to suppress bulging in the portions of the absorbent article 1 that correspond to the interspersed sections 13.

Furthermore, since the densely gathered state of pulp fiber in the interspersed sections 13 is less dense than the densely gathered state around the interspersed sections 13 to the extent of the volume of the empty layers 13b formed in the interspersed sections 13. Therefore, the interspersed section 13 according to the second example also has less rigidity than the area the interspersed section 13. When at least one of such interspersed sections 13 overlaps the fold line, and a longitudinal direction of that interspersed section 13 is aligned with the fold line, the absorbent article 1 can be folded up more easily.

The interspersed section 13 according to the second example is described in further detail. As shown in FIG. 10, a layer thickness of the empty layer 13b is larger than that of the densely gathered layer 13a, and empty space for swelling of SAP is better insured in the interspersed section 13. Here, a layer thickness means a layer thickness in a state in which the absorbent article 1 has been placed horizontally, and the skin face of the absorbent article 1 is facing upward (i.e., the state in FIG. 10). Also as shown in FIG. 10, the accumulated layer 13c is connected to the continuous section 14 on the skin face side. In this manner, since the pulverized pulp is accumulated in an approximately uniform densely gathered state over the entire surface on the skin face side of the absorbent body material 12, it is possible to give the wearer an appropriate feeling of touch when the absorbent article 1 is worn.

To acquire an absorbent body material 12 having the above sort of interspersed section 13, in Step S102 of acquiring the base material 15 of the absorbent body material 12 in the absorbent body production Step S100, a base material 15 is acquired that has concave hole sections 15a that do not pass through from one end side to the other end side in the thickness direction of the base material 15. The base material is placed on the transport apparatus such that an opening of the hole section 15a faces upward, and only SAP is supplied into the hole section 15a (that is, SAP is supplied such that pulp fiber is not mixed into the hole section 15a). At this time, in order to form the empty layer 13b in the interspersed section 13, SAP is supplied into the hole section 15a such that the layer thickness of the densely gathered layer 13a of SAP formed in the hole section 15a is less than a depth of the hole section 15a.

Note that in the above second example, pulp fiber is accumulated in the continuous section 14 and the accumulated layer 13c of the interspersed section. However this is not a limitation. For example, portions corresponding to the continuous section 14 and the accumulated layer 13c of the interspersed section may be formed from a sponge member, sheet-fault resin or the like.

Other Embodiments

Above, based on the above embodiments, an absorbent article according to the invention is described, but the above embodiments of the invention are for facilitating understanding of the invention, and are not limiting of the invention. The invention can of course be altered and improved without departing from the gist thereof, and equivalents are intended to be embraced therein. In particular, embodiments of the invention are not limited by the material qualities of each material described in the above description. Also, in the absorbent body material 12, other than pulp fiber and SAP, granular deodorizing material, granular antibacterial material, granular cooling material, or the like may also be densely gathered. Also, in the above embodiments, the absorbent body 10 was described having a configuration including one absorbent body material 12 in the center in the width direction, but this is not a limitation. For example, a configuration may also be adopted in which side section absorbent bodies are respectively provided along the longitudinal direction at both end sections of the absorbent body 10 in the width direction. Also, a configuration may be adopted in which, instead of side section absorbent bodies, standing gathers are provided respectively at both of those end sections.

Also in the above embodiment, an absorbent article configured to be folded in three for individual wrapping is described. However, this is not a limitation. For example, an absorbent article may be folded in four for individual wrapping (that is, absorbent article in which the folding line position is provided at three locations). Furthermore, although the absorbent article 1 according to the above embodiment is folded up for individual wrapping, this is not a limitation. For example, the absorbent article 1 may be individually wrapped in a state folded in a sideway U-shape.

Also in the above embodiment, a case is described where the fold line formed when the absorbent article 1 is folded up for individual wrapping is aligned with the lateral direction of the absorbent article 1. However, this is not a limitation, and the fold line may be aligned with the longitudinal direction of the absorbent article 1. Furthermore, in the above embodiment, a case is described where the borders between the center section in the longitudinal direction and the end sections in the longitudinal direction of the absorbent article 1 are formed at the forming positions of the fold lines. However, this is not a limitation. The border between the center section in the longitudinal direction and the end section in the longitudinal direction of the absorbent body material 12 may be at a position other than the forming positions of the fold lines.

Also in the above embodiment, a configuration is described in which the interspersed sections 13 are interspersed mainly in the end sections in the longitudinal direction of the absorbent body material 12. However, this is not a limitation. For example, more of the interspersed sections 13 may be interspersed in the center section in the longitudinal direction of the absorbent body material 12 than in the end sections in the longitudinal direction. However, in the absorbent article 1, the portion where the end sections in the longitudinal direction of the absorbent body material 12 are present contacts the abdomen and buttocks of the wearer when the absorbent article 1 is worn. Areas around abdomen and buttocks of the wearer are in a condition in which moisture is easily confined due to perspiration or the like. Therefore, it is necessary to absorb moisture more in abdomen and buttocks by disposing more of SAP in the portion that contacts abdomen and buttocks. With respect to this point, the above embodiment is more desirable.

Also in the above embodiment, a case is described where of the fold lines formed when the absorbent article 1 has been folded up, the interspersed section 13 overlaps only the fold line formed in the further rear end side. However, this is not a limitation. The interspersed section 13 may overlap the fold line in the further front end side as well. In the above embodiment, while two interspersed sections 13 overlap the fold line, this is not a limitation. It is sufficient if at least one interspersed section 13 overlaps the fold line, when the absorbent body 10 is viewed from the skin face. Then, for example, the number of the interspersed sections 13 that overlap the fold line may be greater than that in the above embodiment.

Also in the above embodiment, in the first example, SAP disposed in the interspersed section 13 is dispersed within the interspersed section 13. However, this is not a limitation. For example, SAP in the interspersed section 13 may be disposed locally within the interspersed section 13.

Figure 11:
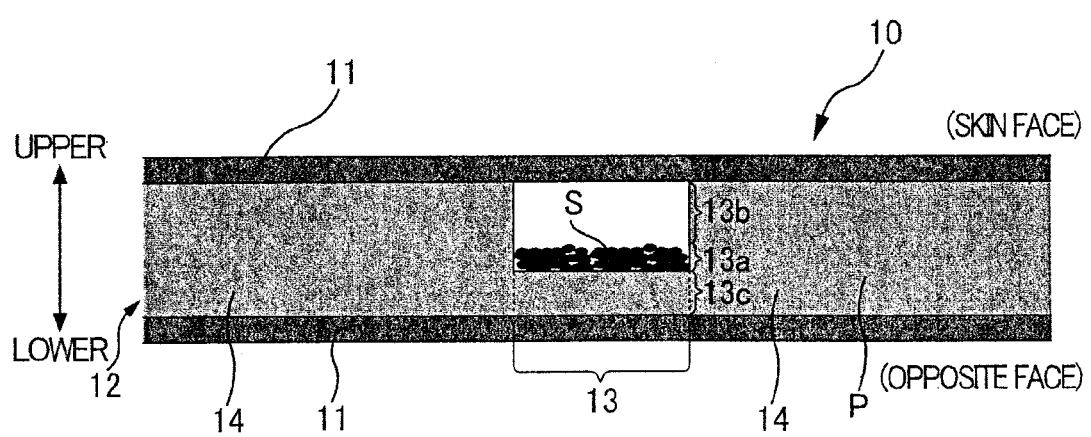
FIG. 11 shows an interspersed section 13 including an accumulated layer 13c of pulp fiber on an opposite face side.
Figure 12:
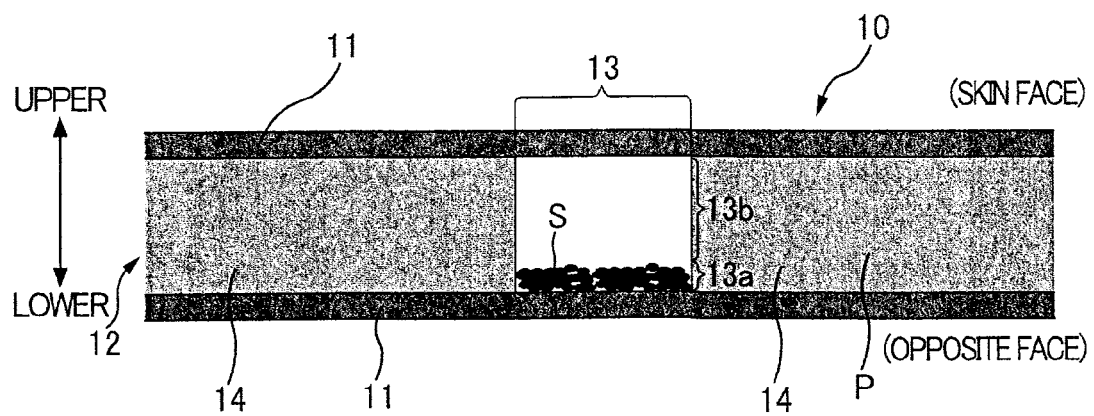
FIG. 12 is a diagram showing an interspersed section 13 including a densely gathered layer 13a and an empty layer 13b only.

On the other hand, in the second example, a configuration is described in which the interspersed section 13 has a three-layer structure and the accumulated layer 13c of pulp fiber is formed on the skin face side. In such a case, as stated above, it is possible to give the wearer of the absorbent article 1 an appropriate feeling of touch. However, this is not a limitation. For example, as shown in FIG. 11, the accumulated layer 13c may be formed in the opposite face side. FIG. 11 is a diagram corresponding to FIG. 10, and shows an interspersed section 13 in which the accumulated layer 13c of pulp fiber is formed in the opposite face side. Note that in FIG. 11, the vertical direction is indicated with an arrow. Furthermore, the interspersed section 13 does not have to have a three-layer structure, and as shown in FIG. 12, the interspersed section 13 may have a two-layer structure configured of the densely gathered layer 13a and the empty layer 13b only. FIG. 12 is a diagram showing an interspersed section 13 including only the densely gathered layer 13a and the empty layer 13b.

Figure 13A:
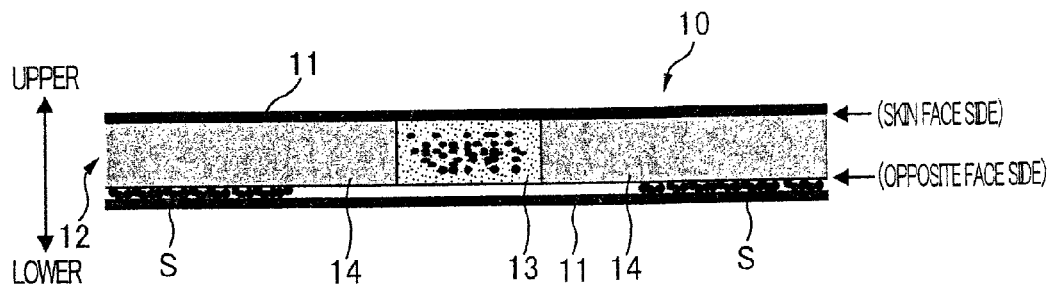
FIG. 13A is a diagram showing an example configuration in which SAP is disposed in portions other than the interspersed section 13 (case 1).
Figure 13B:
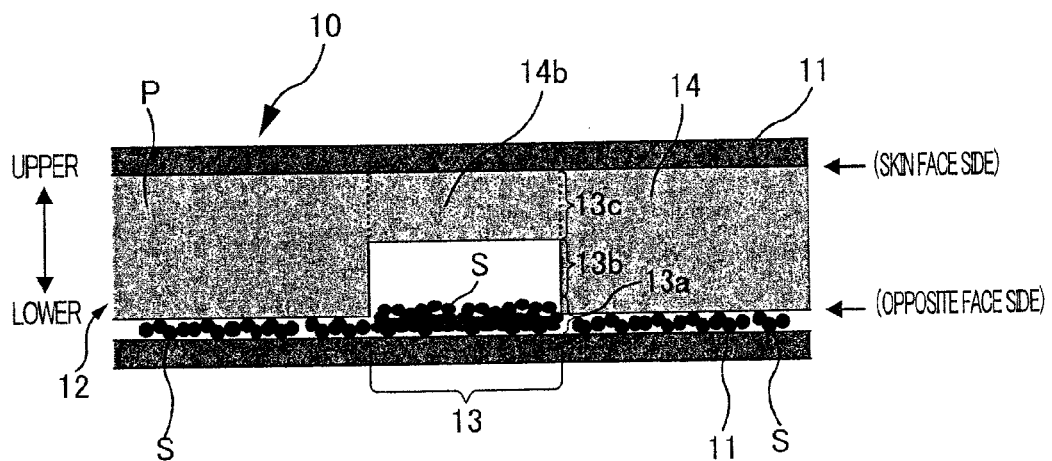
FIG. 13B is a diagram showing an example configuration in which SAP is disposed in portions other than the interspersed section 13 (case 2).
Figure 13C:
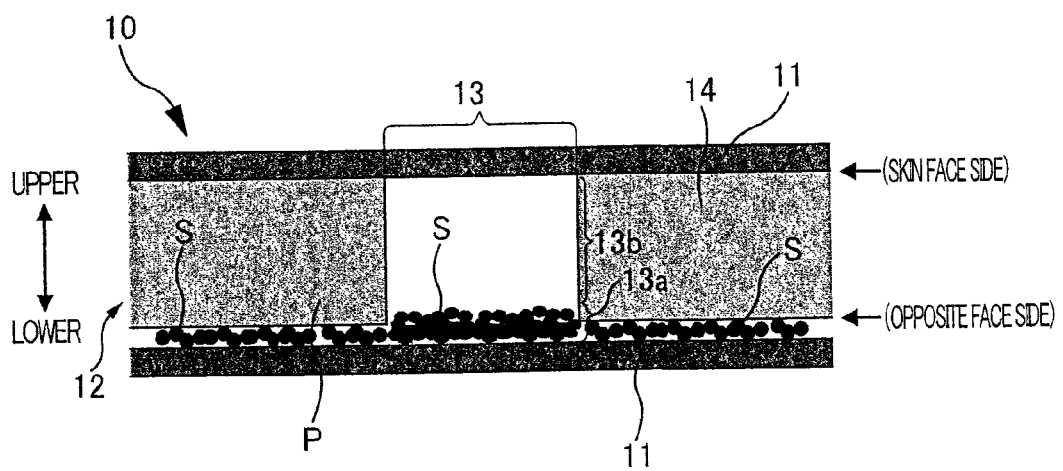
FIG. 13C is a diagram showing an example configuration in which SAP is disposed in portions other than the interspersed section 13 (case 3).

In the above embodiment, SAP in the absorbent body material 12 is disposed mainly within the interspersed section 13. However, this is not a limitation, and SAP may be disposed in a portion other than the interspersed section 13. For example, as shown in FIGS. 13A to 13C, SAP may be built up between the thin paper 11 and a surface of an opposite face side of the absorbent body material 12 (more precisely, a surface of an opposite face side of the continuous section 14). FIGS. 13A to 13C are diagrams respectively showing a configuration in which SAP has been disposed in a portion other than the interspersed section 13. Regarding these example configurations, FIG. 13A shows a case where SAP and pulp fiber are mixed within the interspersed section 13, FIG. 13B shows a case where the interspersed section 13 has a three layer structure configured with the densely gathered layer 13a of SAP, the empty layer 13b, and the accumulated layer 13c of pulp fiber, and FIG. 13C shows a case where the interspersed section 13 has a two layer structure configured with only the densely gathered layer 13a and the empty layer 13b.

Also in the above embodiment, each of the interspersed sections 13 is formed in an oval shape when the absorbent body 10 is viewed from the skin face side (see FIG. 3). However, this is not a limitation. Each of the interspersed sections 13 may be formed in any shape other than an oval shape, so long as it is possible to define the longitudinal direction and lateral direction of each of the interspersed sections 13, when the absorbent body 10 is viewed from the skin face side.

Also in the above embodiment, the deep channel section 22 is formed on the skin face side of the absorbent article 1 by the channel embossing process. The deep channel section 22 extends from the front end section to the rear end section of the absorbent article 1, on both sides of the swelling section 10a. The deep channel section 22 extends to the absorbent body material 12 included in the absorbent body 10, and therefore the channel section 14b that extends from the portion positioned in the front end section to the portion positioned in the rear end section of the absorbent article 1 is formed on the skin face side of the absorbent body material 12 as well. By forming the deep channel section 22 and the channel section 14b as described above, it becomes easy to bend the absorbent article 1 along the longitudinal direction when the absorbent article 1 is worn.

Specifically described, it is easy to fold the absorbent article 1 according to the invention so as to form the fold line in the absorbent article 1 for wrapping. In other words, the front end section and the rear end section of the absorbent article 1 are easy to be bent. On the other hand, the absorbent article 1 is worn in a state bent along the longitudinal direction thereof such that the center section in the width direction of the absorbent article 1 is projected upward. At this stage, if the stated deep channel section 22 and the channel section 14b are formed, the deep channel section 22 and the channel section 14b function as a bend-inducing section, so that it becomes easier to bend the absorbent article 1 along the longitudinal direction thereof. As a result, the absorbent article 1 is worn such that the center section in the longitudinal direction of the absorbent article 1 (more precisely, a portion corresponding to the swelling section 10a of the absorbent article 1) closely contacts the groin of the wearer. Furthermore, since the deep channel section 22 extends from the front end to the rear end of the absorbent article 1 (in other words, the channel section 14b extends from the portion positioned in the front end section to the portion positioned in the rear end section of the absorbent article 1), when the center section in the longitudinal direction of the absorbent article 1 is bent, the end sections follow the center section and are also bent. As a result, the absorbent article 1 is worn in a state appropriately bent (state in which the absorbent article 1 can be closely contacted to the body of the wearer in an appropriate manner).

However, the channel section 14b is not limited to the one extending from the portion positioned in the front end section of the absorbent article 1 to the portion positioned in the rear end section of the absorbent article 1. For example, the channel section 14b may extend from a portion positioned in the center section in the longitudinal direction of the absorbent article 1 to a portion positioned in the rear end section of the absorbent article 1. This is because the front end section of the absorbent article 1 contacts the abdomen of the wearer and therefore the front end section needs not to be bent. Alternatively, a configuration may be adopted in which the channel section 14b is not formed in the absorbent body material 12. However, for the reason described above, it is desirable to form the deep channel section 22 and the channel section 14b.

Also, in the above embodiment, a case is described where the thin paper 11 is included as a covering member that covers the absorbent body material 12. However, this is not a limitation; for example, the absorbent body material 12 does not have to be covered. However, when the absorbent body material 12 is covered, it is possible to prevent SAP densely gathered in the interspersed section 13 from flowing outside the interspersed section 13. With respect to this point, the above embodiment is more desirable.

The invention claimed is:

1. An absorbent article adapted to contact a body of a wearer on a skin face side, said absorbent article comprising:
    an absorbent article main unit having opposite front and rear end sections and a center section between the front and rear end sections in a longitudinal direction of the absorbent article;
    an absorbent body material included in the absorbent article main unit and including absorbent fibers and a super absorbent resin; and
    interspersed sections included in the absorbent body material, each of the interspersed sections having a longitudinal direction, a lateral direction, and a thickness direction,
    wherein
    a densely gathered state of the absorbent fibers in each of the interspersed sections is less dense than a densely gathered state of the absorbent fibers around each of the interspersed sections, and an occupied volume ratio of the super absorbent resin in the interspersed sections is greater than an occupied volume ratio of the super absorbent resin around the interspersed sections,
    the absorbent article has a fold line for wrapping, and at least one of the interspersed sections overlaps the fold line, and the longitudinal direction of the at least one of the interspersed sections is aligned with the fold line,
    the absorbent article main unit further includes sheet sections covering the absorbent body material, and the absorbent fibers accumulated around the interspersed sections are sandwiched between the sheet sections,
    the interspersed sections include first interspersed sections arranged at the front end section and second interspersed sections arranged at the rear end section,
    the interspersed sections are not arranged at the center portion, and
    a number of the second interspersed sections at the rear end section is more than a number of the first interspersed sections at the front end section.

2. An absorbent article according to claim 1, wherein
    the fold line is aligned with a lateral direction of the absorbent article,
    the fold line is formed at a border between the center section and one of the end sections in the longitudinal direction of the absorbent article, and
    the absorbent body material includes a channel section on the skin face side and extending from a portion positioned in the center section of the absorbent article to at least one of the end sections of the absorbent article in the longitudinal direction of the absorbent article.

3. An absorbent article according to claim 1, wherein some of the interspersed sections do not overlap the fold line, and the longitudinal directions of said interspersed sections are inclined with respect to the fold line.

4. An absorbent article according to claim 1, wherein the absorbent body material comprises a compressed portion compressed in a thickness direction of the absorbent article and surrounding a circumferential edge of one of the interspersed sections.

5. An absorbent article according to claim 1, wherein the sheet sections include a top sheet section and a bottom sheet section opposed to the top sheet section, and the interspersed sections protrude beyond surfaces of both the top sheet section and the bottom sheet section outside the interspersed sections.

6. An absorbent article adapted to contact a body of a wearer on a skin face side, said absorbent article comprising:
    an absorbent article main unit having opposite front and rear end sections and a center section between the front and rear end sections in a longitudinal direction of the absorbent article;
    an absorbent body material included in the absorbent article main unit and including absorbent fibers and a super absorbent resin; and
    interspersed sections included in the absorbent body material, and each of the interspersed sections having a longitudinal direction, a lateral direction, and a thickness direction,
    wherein
    the interspersed sections each include a densely gathered layer in which the super absorbent resin is densely gathered, and an empty layer that is adjacent to the densely gathered layer in a thickness direction of the absorbent article,
    the absorbent article has a fold line for wrapping,
    at least one of the interspersed sections overlaps the told line, and the longitudinal direction of the at least one of the interspersed sections is aligned with the fold line,
    the absorbent article main unit further includes sheet sections covering the absorbent body material, and the absorbent fibers accumulated around the interspersed sections are sandwiched between the sheet sections,
    the interspersed sections include first interspersed sections arranged at the front end section and second interspersed sections arranged at the rear end section,
    the interspersed sections are not arranged at the center section, and
    a number of the second interspersed sections at the rear end section is more than a number of the first interspersed sections at the front end section.

7. An absorbent article according to claim 6, wherein
the fold line is aligned with a lateral direction of the absorbent article,
the fold line is formed at a border between the center section and one of the end sections in the longitudinal direction of the absorbent article, and
the absorbent body material includes a channel section on the skin face side and extending from a portion positioned in the center section of the absorbent article to at least one of the end sections of the absorbent article in the longitudinal direction of the absorbent article.

8. An absorbent article according to claim 6, wherein some of the interspersed sections do not overlap the fold line, and the longitudinal directions of said interspersed sections are inclined with respect to the fold line.

9. An absorbent article according to claim 6, wherein each of the interspersed sections further comprises an accumulated layer including the absorbent fibers, said accumulated layer being in direct contact with one of the sheet sections and adjacent to the empty layer and the densely gathered layer in the thickness direction of the absorbent article.

10. An absorbent article according to claim 6, wherein the empty layer is arranged side by side with the densely gathered layer in the thickness direction of the absorbent article.

* * * * *